(12) United States Patent
Cummings et al.

(10) Patent No.: US 6,461,835 B1
(45) Date of Patent: Oct. 8, 2002

(54) FUCOSYLTRANSFERASES, POLYNUCLEOTIDES ENCODING FUCOSYLTRANSFERASES, AND TRANSGENIC MAMMAL INCORPORATING SAME

(75) Inventors: Richard D. Cummings, Edmond, OK (US); Russell A. DeBose-Boyd, Arlington, TX (US); A. Kwame Nyame, Oklahoma City, OK (US)

(73) Assignee: The University of Oklahoma, Oklahoma City, OK (US)

( * ) Notice: Subject to any disclaimer, the term of this patent is extended or adjusted under 35 U.S.C. 154(b) by 0 days.

(21) Appl. No.: 09/390,131

(22) Filed: Sep. 3, 1999

Related U.S. Application Data

(60) Provisional application No. 60/098,922, filed on Sep. 3, 1998.

(51) Int. Cl.[7] .......................... C12P 21/06; C12N 15/00; C12N 5/00; C07H 21/04; C07K 1/00
(52) U.S. Cl. .................. 435/69.1; 435/320.1; 435/325; 435/252.3; 435/455; 435/471; 435/6; 536/23.1; 536/23.2; 536/23.5; 530/350; 530/412
(58) Field of Search ............................. 536/23.2, 23.1, 536/23.5; 435/320.1, 325, 69.1, 6, 455, 471; 530/350, 421

(56) References Cited

PUBLICATIONS

Natsuka et al., Molecular cloning of a cDNA encoding a novel human leukocyte alpha–1,3–fucosyltransferase capable of synthesizing the sialyl lewis x determinant, 1994, Journal of Biological Chemistry, vol. 269, No. 24, pp. 16789–16794.*

Field et al., Molecular cloning of eukaryotic glycoprotein and glycolid glycosyltransferases: a surey, 1995, Glycobiology, vol. 5, No. 5, pp. 463–472.*

DeBose–Boyd et al., Molecular cloning characterization of an alpha 1,3 fucosyltransferase, CEFT–1, from Caenorhabditis elegans, 1998, Glycobiology, vol. 8, No. 9, pp. 905–917.*

* cited by examiner

Primary Examiner—Scott D. Priebe
Assistant Examiner—Sumesh Kaushal
(74) Attorney, Agent, or Firm—Cheryl L. Becker

(57) ABSTRACT

This invention is biological in nature and relates to the synthesis, structure and biological activities of novel α-1,2 and α-1,3 fucosyltransferases from *Caenorhabditis elegans* ("*C. elegans*"). The present invention also contemplates a transgenic non-human eukaryotic mammal whose germ cells and somatic cells incorporate cDNA sequences encoding one or more of the novel α-1,2 and α-1,3 fucosyltransferases from *C. elegans*, introduced into the non-human eukaryotic mammal, or an ancestor of the non-human eukaryotic mammal, at an embyonic stage.

28 Claims, 14 Drawing Sheets

```
FTIII    ----MDPLG--AAKPQWP-------WR------RCLAALLFQLLVAVCFFSYLRVSRDDATGSPR-A  47
bFT      ----MYPPG--CAKVKCS-------WH------HCLPGLLLQLLLALCFFSYLRMSQEKPKPKPM-W  47
cFT-1    --MELGPRWSPAARPGCPRRMR-----------RRWALLGALLGAALALYVCVRELRR--RGS---A  49
CEFT-    MKKQNTPRVFGYYATSCR---WLGVDDRFLRFLWKYLMFACCITYLIVIYAPISKSEQKDW      58

FTIII    PS--GSSRQDT--TPTRPTLLILLLWTWPFHIPVALSRCSEM-----VPGTAD--------CHI    93
bFT      VSELGAPSQATEGSSAHLPLRVLLWTWPFNQPVALSRCSEL-----WPGTAD--------CQL    97
cFT-1    AG----RPEG------EVTVLLWWEPFGRPWRPADCRRR----YNITG---------CLL    86
CEFT-1   KE---GEIELSNDHELDVPILQKEELKPQQRPSFEENVPKKTFNFNPVGKEPFDVEEVL       115

FTIII    IADRKVYPQADTVIVHH----------WDIMSNPK--SRLP--------------PS-------  124
bFT      IVNRSEYPQADAVFVHH----------REVSHRPK--MQLP--------------PS-------  128
cFT-1    SADRGRYGEARAVLFHH----------RDLALHGR--QGLPRG------------PP-------  119
CEFT-1   ISSDIKEERMTATIPGQKRLILSWNAGHSQDNLQGCPDWNCEFTQVRARAPDADAVLI      175

FTIII    -------PRPQGQRWIMWFNLEPPPNCQHLEALDRYFNLIMSYRSDSDIFTPYGWLEPWS      176
bFT      -------PRPADQRWMFSMESPSNCLKLKDLDGYFNLIMSYRDSDIFMPYGWLEPWP        180
cFT-1    -------PRPPRQRWMWMNFESPSHSPGLRGLAGLFNWTMSYRRDSDVFVPYGYLYEP-      170
CEFT-1   AHMDNDFVPKP-NQYVVYFSQESPANSGIQIPRPDVINWTLGFRHDTPAGSPYGYTVKLG     234
```

FIG.5A-1

```
FTIII   GQPAHPPLNLSA------KTELVAMAVSNWKPDSARVRYYQSLQAHLKVDVYG-RSHKPLP  230
bFT     SQPVETLLNISA------KTKLVAMVVSNWNTDSIRVQYYKLLKPHLQVDVYG-RFHTPLP  234
cFT-1   --PSPRPFVLPR------KSRLVAMVISNWNEEHARVRYYRQLKEHLPIDMVG--ARGMALL  222
CEFT-1  AKSRKTGQVVDANLVNGKAKGA

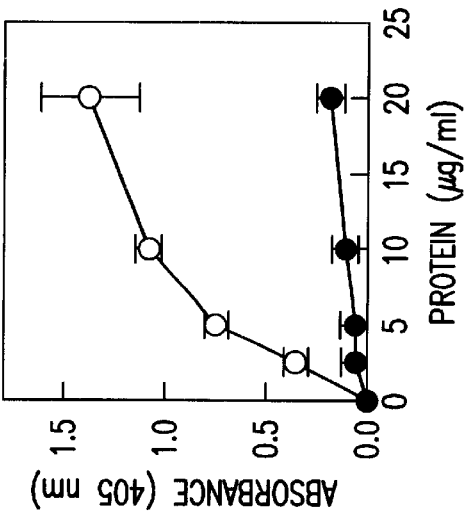
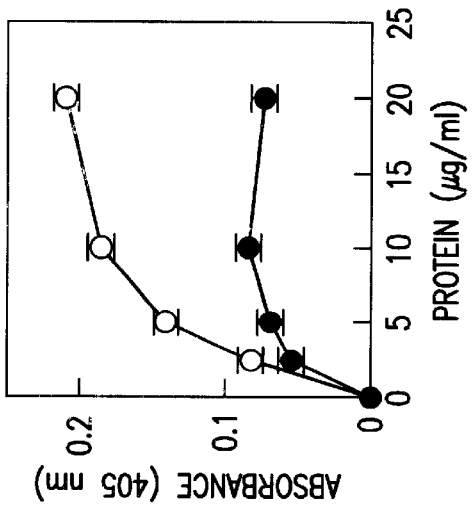
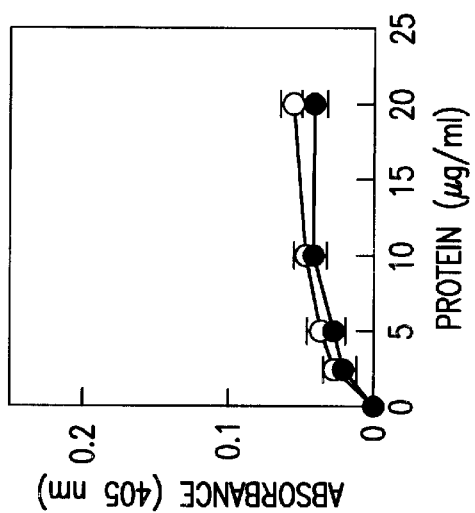
FIG. 9A
FIG. 9B
FIG. 9C

FUCOSYLTRANSFERASES, POLYNUCLEOTIDES ENCODING FUCOSYLTRANSFERASES, AND TRANSGENIC MAMMAL INCORPORATING SAME

CROSS-REFERENCE TO RELATED APPLICATIONS

This application claims priority to the provisional patent application identified by U.S. Serial No. 60/098,922, filed on Sep. 3, 1998, the entire content of which is hereby incorporated herein by reference.

STATEMENT REGARDING FEDERALLY SPONSORED RESEARCH OR DEVELOPMENT

Not applicable.

BACKGROUND OF THE INVENTION

1. Field of the Invention

This invention is biological in nature and relates to the synthesis, structure and biological activities of novel α-1,2 and α-1,3 fucosyltransferases from *Caenorhabditis elegans* ("*C. elegans*"). The present invention also contemplates a transgenic non-human eukaryotic mammal whose germ cells and somatic cells incorporate nucleic acid sequence(s) encoding one or more of the novel α-1,2 and α-1,3 fucosyltransferases from *C. elegans*. The nucleic acid sequence (s) may be introduced into the non-human eukaryotic mammal, or an ancestor of the non-human eukaryotic mammal, at an embyonic stage.

2. Brief Description of Related Art

Glycoconjugates are a class of molecules having a carbohydrate component. Typical glycoconjugates include oligosaccharides; polysaccharides, glycoproteins, glycolipids, glycosaminoglycans, and carbohydrates covalently modifying other molecules, such as steroids, nucleic acids, and xenobiotics. Glycoconjugates having a-linked fucose residues are known in the art to have bioactivity in animals and are required for many cellular functions.

In addition to being important in many biological processes, glycoconjugates are major antigens recognized by the immune systems in higher animals. The pharmaceutical industry has exploited these antigenic properties in order to generate agents that are useful for treating and diagnosing diseases. In particular, pharmaceutical companies have developed recombinant glycoproteins, such as erythropoietin and tissue plasminogen activator, as well as therapeutic oligosaccharides and glycoconjugates, such as Cylexin and glycosylated antibiotics. Glycoconjugates are also important in the nutrition industry for use as food additives and supplements, such as lactose and its derivatives.

A major obstacle in the development, synthesis, and use of glycoconjugates for commercial use is that many glycoconjugates are difficult to synthesize on a commercial level by purely chemical means. Thus, in recent years, there has been increased emphasis on the identification of enzymes, e.g. glycosyltransferases, that can catalyze the formation of specific glycoside attachments to acceptor or substrate molecules both in vitro (e.g. enzyme catalyzed synthesis in the laboratory or production facility), and in vivo (e.g. transgenic animals).

In recent years there has also been an increase in awareness of the fact that glycoconjugates in higher animals and humans which contain the α-fucosylated structures with Fucα1→3GlcNAc-R linkages (where R=H, OH, or an organic molecule) are important in the processes involving cellular adhesion of animal and bacterial cells. Examples of glycans with these linkages are shown in Table I. Some of these α-1,3-fucosylated glycans are found on human leukocytes and are especially important in regulating cellular adhesion events in the early steps of the inflammatory response. Also, α-1-3-fucosylated glycans, such as some of those shown in Table I, are synthesized by *Helicobacter pylori* and other pathogens and may be important in host-parasite interactions.

TABLE I

| Glycans with fucosyl linkages | |
|---|---|
| Lewis x antigen | Galβ1 → 4(Fucα1 → 3)GlcNAc-R (wherein R is defined herein as a carbohydrate, a glycoprotein, or a protein) |
| Lewis y antigen | Fucα1 → 2Galβ1 → 4(Fucα1 → 3)GlcNAc-R |
| Sialyl Lewis x antigen | NeuAcα2 → 3Galβ1 → 4(Fucα1 → 3)GlcNAc-R |
| Fucosylated lacdiNAc antigen | GalNAcβ1 → 4(Fucα1 → 3)GlcNAc-R |
| Fucosylated polylactosamine | Galβ1 → 4(Fucα1 → 3)GlcNAcβ1 → [3Galβ1 → 4(Fucα1 → 3)GlcNAc_β1 → ]$_n$-R, where n = 1 to 1,000 |
| Sialylated and fucosylated polylactosamine | NeuAcα2 → 3(6)Galβ1 → 4(Fucα1 → 3)GlcNAcβ1 → [3Galβ1 → 4(Fucα1 → 3)GlcNAc_β1 → ]$_n$-R, where n = 1 to 1,000 |
| O(H)-Blood group antigen | Fucα1 → 2Galβ1 → 3(4)GlcNAc-R |
| Lewis a antigen | Galβ1 → 3(Fucα1 → 4)GlcNAc-R |
| Sialyl Lewis a antigen | NeuAcα2 → 3Galβ1 → 3(Fucα1 → 4)GlcNAc-R |
| Lewis b antigen | Fucα1 → 2Galβ1 → 3(Fucα1 → 4)GlcNAc-R |
| A-Blood group antigen | GalNAcα1 → 3(Fucα1 → 2)Galβ1 → 3(4)GlcNAc-R |
| B-Blood group antigen | Galα1 → 3(Fucα1 → 2)Galβ1 → 3(4)GlcNAc-R |

In order to commercially exploit glycoconjugates and their unique functional abilities, it has been necessary to scale up the synthesis of glycans containing α-1,3-, and α-1,2-fucosylated glycans. These synthesized glycans can then be used as inhibitors of cell adhesion mediated by glycoconjugates containing these linkages. For example, the commercial production of α-1,3-fucosylated glycans is ongoing in some pharmaceutical companies throughout the developed world and is expected to be a major pharmaceutical contribution in the coming years.

Because of the difficulty and costs in purely chemical synthetic methods for carbohydrate production, commercial production of α-1,3-, α1,4- and α-1,2-fucosylated glycans has historically been dependent upon recombinant enzymes or α-fucosyltransferases, which exhibit specific abilities to catalyze the appropriate linkages. These types of reactions are shown generally in Table II. Each of the α-fucosyltransferases thus far identified in the art have limitations in the types of acceptors utilized, the rate of product formation, as well as potential undesirable side effects. For example, a human α-fucosyltransferase termed Fuc-T-IV acts with the best efficiency toward non-sialylated acceptors and acts relatively poorly with sialylated acceptors. Also, another enzyme, termed Fuc-TIII, can catalyze both α-1,3- and α-1,4-linkages to GlcNAc residues in the two different acceptors.

These and other objects of the present invention will become apparent in light of the present specification, drawings, and claims.

It is still another object of the present invention to provide for the production of recombinant proteins from fucosyltransferases or products requiring action by fucosyltransferases in a non-human eukaryotic mammal's milk.

These and other features and advantages of the invention will be apparent given the present specification, figures, embodiments and claims.

SUMMARY OF THE INVENTION

Novel and previously unidentified α-fucosyltransferases have been identified, isolated and purified from the *C.*

TABLE II
Reactions involving fucosyltransferases

| | α1, 3-Fuc-T | |
|---|---|---|
| GDP-Fucose + Galβ1 ⟶ 4)GlcNAc—R [donor] [acceptor] | ⟶ Galβ1 ⟶ 4(Fucα1 ⟶ 3)GlcNAc—R + GDP [Le$^X$ product] | |
| | α1, 4-Fuc-T | |
| GDP-Fucose + Galβ1 ⟶ 3)GlcNAc—R [donor] [acceptor] | ⟶ Galβ1 ⟶ 3(Fucα1 ⟶ 4)GlcNAc—R + GDP [Le$^a$ product] | |
| | α1, 2-Fuc-T | |
| GDP-Fucose + Galβ1 ⟶ 4)GlcNAc—R [donor] [acceptor] | ⟶ Fucα1 ⟶ 2Galβ1 ⟶ 4)GlcNAc—R + GDP [O(OH) product] | |

Therefore, it is an object of the present invention to disclose and claim fucosyltransferases isolated and purified from *C. elegans* nematode, and in particular α-1,3-, and α-1,2-fucosyltransferases isolated and purified from *C. elegans*.

The present invention further contemplates homologous variants of said α-1,3 and α-1,2 fucosyltransferases and nucleic acids which encode said fucosyltransferases.

It is also an object of the present invention to disclose and claim a transgenic mammal, such as a cow or goat, incorporating the genes or cDNA encoding the α-1,3- and α-1,2-fucosyltransferases isolated and purified from *C. elegans* and said homologous versions thereof.

elegans nematode. These novel *C. elegans* fucosyltransferases, described further herein, have been used to generate α-fucosylated glycoconjugates. In particular, the *C. elegans* nematode contains fucosyltransferases which catalyze the reactions shown in Table III. The amino acid and nucleotide sequences for the novel α1,3- and α1,2-fucosyltransferases found in *C. elegans* can be found in SEQ ID NO:1 and SEQ ID NO:2, respectively.

The present invention also includes a transgenic non-human eukaryotic mammal whose germ cells and somatic cells incorporate nucleic acid sequence(s) encoding one or more of the novel α1,3 and α1,2-fucosyltransferases from *C. elegans*.

TABLE III
Reactions catalyzed by fucosyltransferases from C. elegans (Reaction A)

$$\text{GDP-Fucose} + \text{Gal}\beta1 \longrightarrow 4\text{GlcNAc}\text{—R} \xrightarrow{\alpha1,3\text{-Fuc-T}} \text{Gal}\beta1 \longrightarrow 4(\text{Fuc}\alpha1 \longrightarrow 3)\text{GlcNac}\text{—R} + \text{GDP}$$
[donor]   [acceptor]   [Le$^x$ product]

(Reaction B)

$$\text{GDP-Fucose} + \text{NeuAc}\alpha2 \longrightarrow 3\text{Gal}\beta1 \longrightarrow 4\text{GlcNAc}\text{—R} \xrightarrow{\alpha1,3\text{-Fuc-T}} \text{NeuAc}\alpha2 \longrightarrow 3\text{Gal}\beta1 \longrightarrow 4(\text{Fuc}\alpha1 \longrightarrow 3)\text{GlcNac}\text{—R} + \text{GDP}$$
[donor]   [acceptor]   [sialyl product]

(Reaction C)

$$\text{GDP-Fucose} + \text{GalNAc}\beta1 \longrightarrow 4\text{GlcNAc}\text{—R} \xrightarrow{\alpha1,3\text{-Fuc-T}} \text{GalNAc}\beta1 \longrightarrow 4(\text{Fuc}\alpha1 \longrightarrow 3)\text{GlcNac}\text{—R} + \text{GDP}$$
[donor]   [acceptor]   [LDNF product]

(Reaction D)

$$\text{GDP-Fucose} + \text{Gal}\beta1 \longrightarrow 3\text{Glc(NAc)}\text{—R} \xrightarrow{\alpha1,2\text{-Fuc-T}} \text{Fuc}\alpha1 \longrightarrow 2\text{Gal}\beta1 \longrightarrow 3\text{Glc(Nac)}\text{—R} + \text{GDP}$$
[donor]   [acceptor]   [O(OH) product]

(Reaction E)

$$\text{GDP-Fucose} + \text{Gal}\beta1 \longrightarrow 3\text{GlcNAc}\text{—R} \xrightarrow{\alpha1,4\text{-Fuc-T}} \text{Gal}\beta1 \longrightarrow 3(\text{Fuc}\alpha1 \longrightarrow 4)\text{GlcNac}\text{—R} + \text{GDP}$$
[donor]   [acceptor]   [Le$^x$ product]

BRIEF DESCRIPTION OF THE DRAWINGS

FIGS. 5A–5B is a graphical comparison of the protein sequences of CEFT-1 with vertebrate α1,3 FTs (SEQ ID NO:3, SEQ ID NO:6, SEQ ID NO:7, SEQ ID NO:8 and SEQ ID NO:10).

FIGS. 9A–9C graphically depict the reactivity of CEFT-1-transfected COS7 cells with anti-Le$^x$ antibodies.

DETAILED DESCRIPTION OF THE INVENTION

Figure 1:
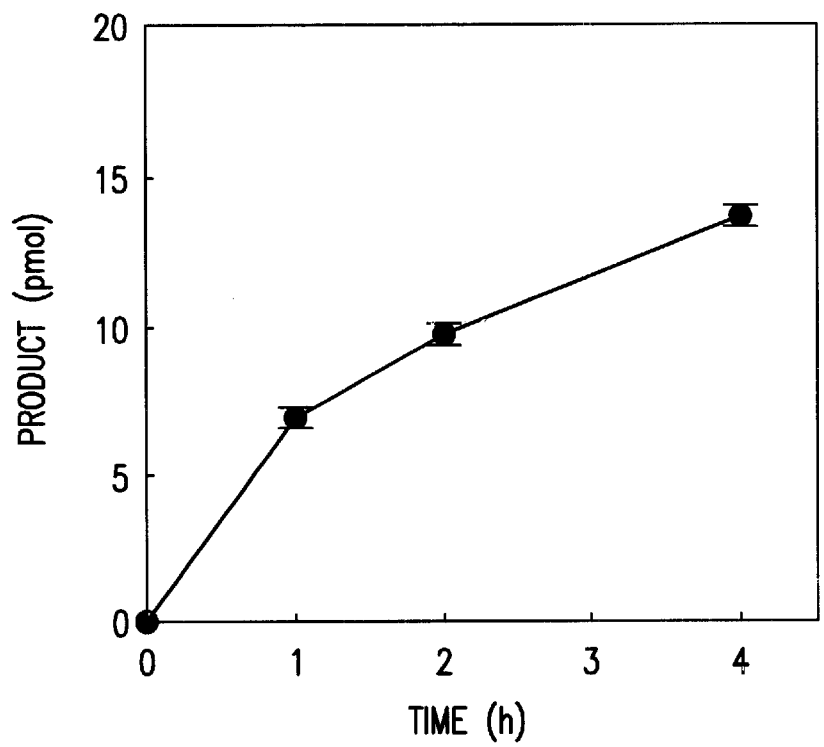
FIG. 1 graphically depict fucosyltransferase activity in *C. elegans* homogenates.
Figure 1:
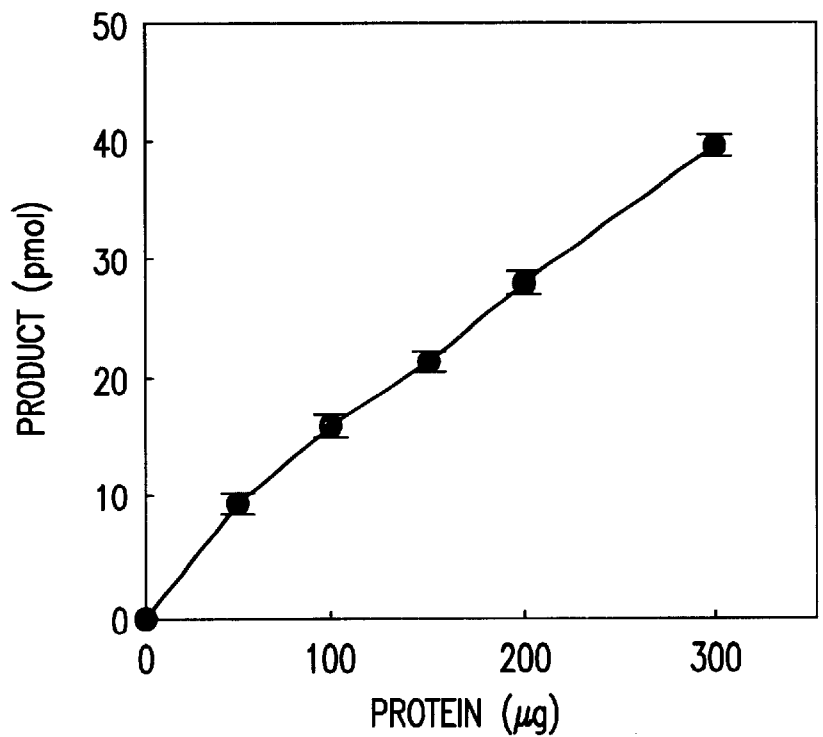

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Since *C. elegans* contains the afore-mentioned novel, and previously unidentified fucosyltransferases, a search was made for the gene or genes encoding them. The genomic sequence of *C. elegans* is available worldwide via a genomic sequence database headquartered at Washington University in St. Louis, Mo. This genomic database was searched in order to determine gene candidates for the novel *C. elegans* α-fucosyltransferases. This search utilized a 4–5 amino acid peptide segment to search through the database in order to find a gene "hit". The search revealed several "candidate" α-fucosyltransferase genes. None of the genes discovered in *C. elegans* which encode for α-fucosyltransferases displayed close sequence identity to any of the known α-fucosyltransferase genes in other animals: i.e. the closest match was no more than approximately 25% in identity.

After identifying the candidate α-fucosyltransferase genes in the *C. elegans* database, reverse transcriptase-polymerase chain reaction (RT-PCR) on total messenger RNA (mRNA) from adult *C. elegans*, using forward and reverse primers matching the known sequences of the genes in question, was performed. The RT-PCR product for one of the genes was identified, subcloned, sequenced and placed in an appropriate mammalian expression vector by commonly used techniques known in the molecular biology art. This gene was termed C. elegans α-fucosyltransferase-1 or CEFT-1.

The cDNA encoding CEFT-1 was expressed in a monkey kidney cell line named COS-7. The transfected cells produced the enzyme and the transfected cell extracts contained an α-1,3-fucosyltransferase activity that reacted as shown in sections A–C of Table III hereinabove. In order to confirm the expression of the recombinant enzyme, a rabbit antisera was raised to a recombinant form of the enzyme expressed as a glutathionine-S-transferase (GST) fusion protein in E. coli. The antibody generated to the GST-CEFT-1 fusion protein reacted strongly in Western blot with extracts from COS-7 cells transfected with the cDNA encoding CEFT-1, whereas there was no reaction with the non-transfected control cells.

CEFT-1 shows little activity toward sialylated acceptors. The present invention does reveal, however, that C. elegans demonstrates activity toward α-1,3-fucosylation of sialylated acceptors which indicates the presence of at least one other α-1,3-fucosyltransferase that can utilize sialylated acceptors efficiently, as shown in Table III.

An α-1,2-fucosyltransferase that can synthesize the O(H) antigen was also identified in an extract of C. elegans. Using the strategy outlined briefly above and in more depth hereinafter for CEFT-1, the α-1,2-fucosyltransferase present in C. elegans was identified and its genes and cDNA were cloned to generate a recombinant form of the α-1,2-fucosyltransferase. The α-1,2-fucosyltransferase from extracts of C. elegans was purified using the assay described herein. From the purified α-1,2-fucosyltransferase protein the amino acid sequence was obtained and this sequence information was used to identify a cDNA cable of encoding the α-1,2-fucosyltransferase. Molecular probes for cloning the gene and cDNA encoding the α-1,2-fucosyltransferase in C. elegans were also designed.

The recombinant form of CEFT-1, as well as the other α-1,3- and α-1,2-fucosyltransferases isolated from C. elegans, were prepared by recombinant means using cDNA encoding these enzymes, is contemplated for use for in vitro synthesis of α-1,3- and α-1,2-fucosylated glycans, including but not limited to those shown in Table I, by using isolated or partly purified recombinant enzymes or by expressing these enzymes in heterologous host cells to allow their action on newly synthesized glycoconjugates in the host cells. In addition, the genes or cDNA encoding the C. elegans α-1,3- and α-1,2-fucosyltransferases can be expressed transgenically in tissues and organs of animals, e.g. mammary gland and liver, thereby allowing the production of α-1,3- and/or α-1,2-fucosylated glycans in vivo as described in the references cited hereinbelow.

Transgenic animals carry a gene which has been introduced into the germline of the animal, or an ancestor of the animal, at an early (usually one-cell) developmental stage. For example, Wagner et al. (1981) P.N.A.S. U.S.A. 78, 5016; and Stewart et al. (1982) Science 217, 1046 describe transgenic mice containing human globin genes; Constantini et al. (1981) Nature 294, 92, and Lacy et al. (1983) Cell 34, 343 describe transgenic mice containing rabbit globin genes; McKnight et al. (1983) Cell 34, 335 describes transgenic mice containing the chicken transferrin gene; Brinster et al. (1983) Nature 306, 332 describes transgenic mice containing a functionally rearranged immunoglobulin gene; Palmiter et al. (1982) Nature 300, 611 describes transgenic mice containing the rate growth hormone gene fused to a heavy metal-inducible metalothionein promoter sequence; Palmiter et al. (1982) Cell 29, 701 describes transgenic mice containing a thymidine kinase gene fused to a metalothionein promoter sequence; Palmiter et al. (1983) Science 222, 809 describes transgenic mice containing the human growth hormone gene fused to a metalothionein promoter sequence; and U.S. Pat. No. 4,873,191 describes genetic transformation of zygotes. These references are herein expressly incorporated by reference in their entirety.

Such transgenic expression of a heterologous α-1,2-fucosyltransferase in mice mammary gland has been documented by Prieto, et al. "Remodeling of Mouse Milk Glycoconjugates by Transgenic Expression of a Human Glycosyltransferase," J. Biol. Chem. (1995) 270, 29515–29519, which is also herein expressly incorporated by reference in its entirety.

Recombinant DNA technology has enabled the cloning and expression of genes encoding medically and agriculturally important proteins and glycoproteins. Such products include, for example, insulin, growth hormone, growth hormone releasing factor, somatostatin, tissue plasminogen activator, tumor necrosis factor, lipocortin, coagulation factors VIII and IX, the interferons, colony stimulating factor, the interleukins and urokinase.

Many of these important proteins, however, are large (molecular weights in excess of 30 Kd), secreted, require sulfhydryl bonds to maintain proper folding, are glycosylated and are sensitive to proteases. As a result, the recombinant production of such products in prokaryotic cells has proven to be less than satisfactory because the desired recombinant proteins are incorrectly processed, lack proper glycosylation or are improperly folded. Accordingly, resort has been had to the production of those recombinant prokaryotic cells. This technique has proven to be both expensive and often unreliable due the variability of cell culture methods. For example, average yields are 10 mg of recombinant protein per liter of culture media, with the resulting cost typically far exceeding $1,000 per gram of recombinant protein. Accordingly, resort has been had to the production of those recombinant proteins in cultured eukaryotic cells.

The present invention solves such problems by providing an efficient means of producing large quantities of recombinant enzyme products in the milk of transgenically altered mammals. According to this invention, a DNA sequence coding for a desired C. elegans fucosyltransferase protein is operatively linked in an expression system to a milk-specific protein promoter, or any promoter sequence specifically activated in mammary tissue, through a DNA sequence coding for a signal peptide that permits secretion and maturation of the desired protein or milk component (e.g. a carbohydrate) in the mammary tissue. More preferably, the expression system also includes a 3' untranslated region downstream of the DNA sequence coding for the desired recombinant protein. This untranslated region may stabilize the rDNA transcript of the expression system. Optionally, the expression system also includes a 5' untranslated region upstream of the DNA sequence coding for the signal peptide.

The expression system is transgenically introduced into a host genome by standard transgenic techniques. As a result, one or more copies of the construct or system becomes incorporated into the genome of the transgenic mammal. The presence of the expression system will permit the female species of the mammal to produce and to secrete the recombinant protein product, into or along with its milk. Such method permits the low cost, high level production of the desired proteins.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains α1,2 or α1,3 fucosyltransferase coding sequence yet is isolated away from, or purified free from unrelated genomic DNA, for example, a total C. elegans. Included within the term "DNA segment", are DNA segments and smaller fragments of such segments, and also recombinant vectors, including, for example, plasmids, cosmids, phage, viruses, and the like.

Similarly, a DNA segment comprising an isolated or purified α1,2 or α1,3 fucosyltransferase gene refers to a DNA segment including α1,2 or α1,3 fucosyltransferase coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the genes of interest, in this case α1,2 or α1,3 fucosyltransferase, form the significant part of the coding region of the DNA segment, and that the DNA segment does not contain large portions of naturally-occurring coding DNA. Of course, this refers to the DNA segment as originally isolated, and does not exclude genes or coding regions later added to, or intentionally left in the segment by the hand of man.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences which encode an α1,2 or α1,3 fucosyltransferase gene, that includes within its amino acid sequence an amino acid sequence in accordance with SEQ ID NO:1 and SEQ ID NO:2. Moreover, in other particular embodiments, the invention concerns isolated DNA segments and recombinant vectors incorporating DNA sequences which encode a gene that includes within its amino acid sequence the amino acid sequence of an α1,2 or α1,3 fucosyltransferase gene or DNA, and in particular to an α1,2 or α1,3 fucosyltransferase gene or cDNA, corresponding to C. elegans α1,2 or α1,3 fucosyltransferase. For example, where the DNA segment or vector encodes a full length α1,2 or α1,3 fucosyltransferase protein, or is intended for use in expressing the α1,2 or α1,3 fucosyltransferase, preferred sequences are those which are essentially as set forth in SEQ ID NOS:1 and 2.

The art is replete with examples of practitioners ability to make structural changes to a nucleic acid segment (i.e. encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1029–1029 (1988) [" . . . according to the observed exchangeability of amino acid side chains, only four groups could be delineated; (i) Ile and Val; (ii) Leu and Met, (iii) Lys, Arg., and Gln, and (iv) Tyr and Phe."]; (2) Niefind et al. "Amino Acid Similarity Coefficients for Protein Modeling and Sequence Alignment Derived from Main-Chain Foling Anoles." J. Mol. Biol. 219:481–497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216–226 (1992) ["Analysis of the pattern of observed substitutions as a function of local environment shows that there are distinct patterns . . . " Compatible changes may be made."]

These references and countless others, indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding enzymatically active α1,2 or α1,3 fucosyltransferase. Thus, one of ordinary skill in the art would appreciate that substitutions can be made to the α1,2 or α1,3 fucosyltransferase nucleic acid segments listed in SEQ ID NO:1 and SEQ ID NO:2 without deviating outside the scope and claims of the present invention. Standardized and accepted functionally equivalent amino acid substitutions are presented in Table IV.

TABLE IV

| Amino Acid Group | Conservative and Semi-Conservative Substitutions |
|---|---|
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

As used herein, the term "recombinant vector" refers to a vector that has been modified to contain a nucleic acid segment that encodes an α1,2 or α1,3 fucosyltransferase. The recombinant vector may be further defined as an expression vector comprising a promoter operatively linked to said α1,2 or α1,3 fucosyltransferase.

Nucleic acid molecules encoding amino acid sequence variants of α1,2 or α1,3 fucosyltransferase are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of a DNA molecule encoding an earlier prepared variant or a non-variant version of α1,2 or α1,3 fucosyltransferase polypeptide.

Oligonucleotide-mediated mutagenesis is one preferred method for preparing amino acid substitution variants of α1,2 or α1,3 fucosyltransferase. This technique is well known in the art as described by Adelman et al., *DNA*, 2, 183 (1983), which is herein expressly incorporated by reference in its entirety. Briefly, α1,2 or α1,3 fucosyltransferase DNA is altered by hybridizing an oligonucleotide encoding the desired mutation to a DNA template, where the template is the single-stranged form of a plasmid or bateriophage containing the unaltered or native DNA sequence of α1,2 or α1,3 fucosyltransferase. After hybridization, a DNA polymerase is used to synthesize an entire second complementary strand of the template that will thus incorporate the oligonucleotide primer, and will code for the selected alternation in the α1,2 or α1,3 fucosyltransferase.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75 5765 (1978), which is herein expressly incorporated by reference in its entirety.

The DNA template can be generated by those vectors that are either derived from bateriophage M13 vectors (the commercially available M13mp18 and M 13mp19 vectors are suitable), or those vectors that contain a single-stranded phage origin of replication as described by Viera et al., *Meth. Enzymol.* 153, 3 (1987), which is herein expressly incorporated by reference in its entirety. Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989). Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the α1,2 or α1,3 fucosyltransferase, and the other strand (the original template) encodes the native, unaltered sequence of the α1,2 or α1,3 fucosyltransferase, respectively. This heteroduplex molecule is then transformed into a suitable host cell, usually a prokaryote cell. The isolated region is then removed and placed in an appropriate vector for protein production, generally an expression vector of the type typically employed for transformation of an appropriate host.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it effects the transcription of the sequence; or a ribosome binding site is operably linked to a coding sequence if it is positioned so as to facilitate translation. Generally, "operably linked" means that DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistant genes, such as neo, hpt, bar, aroa, dapa and the like.

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction, and is herein expressly incorporated by reference for these teachings.

Terminal Fucα1→GlcNAc linkages are critical components in the molecular events underlying a variety of biological phenomena, such as the adhesion of activated leukocytes to inflamed endothelium, embryogenesis, immune responses, and cancer metastasis. These fucosylated determinants, occurring in the Lewis X (Le$^x$)[1] and sialyl Le$^x$ angtigens, are displayed in a tissue and/or cell-type specific manner, due in part to the restricted expression of the glycosyltransferases, especially the α1,3 fucosyltransferases ("α1,3FT") involved in their biosynthesis. Several α1,3FTs have been identified and characterized from both vertebrates, invertebrates and in prokaryotes. Thus, molecular cloning has revealed an emerging family of α1,3FTs.

The presently disclosed α1,3 fucosylated glycans and α1,3FTs stem from observations that many helminthic parasites, such as *Schistosoma mansoni, Dirofilaria immitis*, and *Haemonchus contortus*, synthesize antigenic protein and lipid-associated glycoconjugates in which Fucα1→3GlcNAc is a major determinant. Several of these antigenic glycans are high molecular weight N-glycans containing polylactosamine [→3Galβ1→4GlcNAcβ1→]$_n$ in which most of the inner GlcNAc residues in the repeating units are α1,3 fucosylated and the elongated glycans are capped by the Le$^x$ antigen, Galβ1→4[Fucα1→3]GlcNAc, at the nonreducing terminus. Some of the—and O-glycans in both *S. mansoni* and *D. immitis* also contain fucosylated lacdiNAc (LDN) structures GalNAcβ1→4[Fucα1→3] GlcNAc. It has been proposed that the immune responses generated toward fucosylated glycans may play a role in the pathogenesis of schistosomiasis.

Previously an α1,3FT, in crude extracts of adult schistosomes and adult *H. contortus* that can synthesize α1,3 fucosylated glycans, was identified. The α1,3FTs display enzymatic properties that closely resemble those of human FTIV, which is expressed in myeloid cells. These studies provided the background for searching other helminths for the expression of an α1,3FT and/or the expression of Le$^x$ glycoconjugates.

The free-living nematode, *Caenorhabditis elegans*, expresses an α1,3FT activity capable of synthesizing Le$^x$-containing glycoconjugates in vitro. Characterization of the enzymatic properties of the *C. elegans* α1,3FT reveal it to be similar in many enzymatic properties to the α1,3FT expressed by *H. contortus* and schistosomes. A search of the *C. elegans* genome database revealed a candidate gene, named CEFT-1, which has sequence similarities to known α1,3FTs. The cDNA was cloned and expression of the recombinant enzyme reveals that it is an α1,3FT and can promote Le$^x$, but not sialyl Le$^x$, expression in transfected COS7 cells.

The present invention comprises α-1,3 fucosyltransferases and α-1,2 fucosyltransferases purified from *C. elegans* and cDNAs that encode these enzymes, for example CEFT-1. The *C. elegans* CEFT-1 cDNA comprises 1353 base pairs and encodes a protein of 451 amino acids. The invention further comprises a second *C. elegans* fucosyltransferase designated herein as an α-1,2 fucosyltransferase which has a cDNA comprising 1068 base pairs and encodes a protein of 356 amino acids. The invention further comprises homologous proteins encoded by homologous cDNAs, homologous cDNAs, vectors and host cells which express the cDNAs, and methods of using the *C. elegans* fucosyltransferases and cDNAs which encode them.

In further aspects, the present invention contemplates cloning vectors, which comprise the nucleic acid of the invention and prokaryotic or eukaryotic expression vectors, which comprise the nucleic acid molecule of the invention, operatively associated with an expression control sequence. Accordingly, the invention further relates to a bacterial or mammalian cell transfected or transformed with an appropriate expression vector.

In yet a further aspect, the invention is directed to an antibody that binds to the fucosyltransferases described herein. Such an antibody can be a polyclonal or a monoclonal antibody. The invention is also directed to antibodies that bind to a ligand binding site of the fucosyltransferase.

Accordingly, the present invention contemplates a nucleic acid, in particular a DNA, that encodes a novel *C. elegans* fucosyltransferase or a fragment, or homologous derivative or analog thereof. The invention further contemplates producing an expression system comprising a fucosyltransferase encoding polynucleotide.

The polynucleotides of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown herein or may be a different coding sequence which, as a result of the redundancy or degeneracy of the genetic code, encodes the same, mature polypeptide as the DNA coding sequences shown herein.

The polynucleotides which encode for the mature polypeptides may include: only the coding sequence for the mature polypeptide; the coding sequence for the mature polypeptide and additional coding sequence such as a leader or secretory sequence or a proprotein sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only a coding sequence for the polypeptide as well as a polynucleotide which includes additional coding and/or non-coding sequences.

The present invention further relates to variants of the hereinabove described polynucleotides which encode fragments, analogs and derivatives of the polypeptide having SEQ ID NO:1 and SEQ ID NO:2, and which encode fragments, analogs, and derivatives of the *C. elegans* α-1, 2-fucosyltransferase and α1,3-fucosyltransferase described elsewhere herein. The variants of the polynucleotide may be naturally occurring allelic variants of the polynucleotides or nonnaturally occurring variants of the polynucleotides.

Thus, the present invention includes polynucleotides encoding the same mature polypeptide as shown in SEQ ID NO:1 and SEQ ID NO:2 as well as variants of said polynucleotide which variants encode for a fragment, derivative or analog of said polypeptide. Such nucleotide variants include deletion variants, substitution variants and addition or insertion variants.

As hereinabove indicated, the polynucleotides may have a coding sequence which is a naturally occurring allelic variant of the coding sequences shown in SEQUENCE ID NO:1 and SEQ ID NO:2. As known in the art, an allelic variant is an alternate form of a polynucleotide sequence which may have a substitution, deletion or addition of one or more nucleotides, which does not substantially alter the function of the encoded polypeptide.

The terms "fragment," "derivative," and "analog" when referring to the polypeptides of SEQ. ID NO:1 and SEQ ID NO:2 or to the other α1,2 or α1,3 fucosyltransferase described herein means a polypeptide which retains essentially the same biological function or activity as an α-1,2 or α-1,3 fucosyltransferase. Thus, an analog includes a proprotein which can be activated by cleavage of a proprotein portion to produce an active mature polypeptide. The polypeptides of the present invention may also be a natural polypeptide or a synthetic polypeptide, or preferably a recombinant polypeptide of a C. elegans fucosyltransferase.

The fragment, derivative or analog of the fucosyltransferase described herein may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

The polypeptides and polynucleotides of the present invention may be provided in an isolated form, and preferably are purified to homogeneity. The term "isolated" means that the material is removed from its original environment (e.g., the natural environment if it is naturally occurring). For example, a naturally-occurring polynucleotide or polypeptide present in a living animal is not isolated, but the same polynucleotide or polypeptide separated from some or all of the coexisting materials in the natural system, is isolated. Such polynucleotides could be part of a vector and/or such polynucleotides or polypeptides could be part of a composition, and still be isolated in that such vector or composition is not part of its natural environment. The present invention also relates to vectors which include polynucleotides of the present invention, host cells and animals which are genetically engineered with vectors of the invention and the production of polypeptides of the invention by recombinant techniques.

Host cells are genetically engineered (transduced, transformed or transfected) with the vectors of this invention, such as, a cloning vector or an expression vector. The vector may also be in the form of a plasmid, a viral particle, or a phage or other vectors known in the art. The engineered host cells can be cultured in conventional nutrient media modified as appropriate for activating promoters, selecting transformants or amplifying the fucosyltransferase genes. The culture conditions, such as temperature, pH and the like, are those previously used with the host cell selected for expression, and will be apparent to the ordinary skilled artisan.

The fucosyltransferase encoding polynucleotides of the present invention may be employed for producing fucosyltransferases by recombinant techniques. The vector may include the fucosyltransferase polynucleotide and a gene encoding a protein requiring fucosylation or a gene encoding an enzyme which produces a molecule such as a carbohydrate or peptide which requires fucosylation. Such vectors include chromosomal, nonchromosomal and synthetic DNA sequences such as derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable in the host. The appropriate DNA sequence (or sequences) may be inserted into the vector by a variety of procedures. For example, the DNA sequence can be inserted into an appropriate restriction endonuclease sites by procedures known in the art.

The DNA sequence in the expression vector is preferably operatively linked to an appropriate expression control sequence(s) (promoter) to direct mRNA synthesis. As representative examples of such promoters, there may be mentioned: LTR or SV40 promoter, the E. coli lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

The vector containing the appropriate DNA sequence as hereinabove described, as well as an appropriate promoter or control sequence, may be employed to transform an appropriate host to permit the host to express the protein as described elsewhere herein in a method well known to those of ordinary skill in the art.

Bacterial cells, such as E. coli, Streptomyces, Salmonella typhimurium; fungal cells, such as yeast; insect cells such as Drosophila and Sf9; animal cells such as CHO, COS or Bowes melanoma and plant cells are representative examples of appropriate hosts. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment the construct further comprises regulatory sequences such as a promoter operably linked to the sequence. Large numbers of suitable vectors and promoters are known to those of ordinary skill in the art and include, but not by way of limitation—bacterial; such as pQE70, pQE60, pQE-9 (Qiagen), pbs, pD10, phagescript, psiX174, pbluescript SK, pbsks, pNH8A, pNH16a, pNH18A, pNH46A (Stratagene), ptrc99a, pKK223-3, pKK233-3, pDR540, pRIT5 (Pharmacia); and Eukaryotic; such as pWLNEO, pSV2CAT, pOG44, pXT1, pSG (Stratagene) pSVK3, pBPV, pMSG, pSVL (Pharmacia). However, any other plasmid or vector may be used as long as they are replicable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. Suitable host cells include prokaryotic or lower or higher eukaryotic organisms or cell lines, for example bacterial, mammalian, yeast, or other fungi, viral, plant or insect cells. Methods for transforming or transfecting cells to express foreign DNA are well known in the art. See for example, Itakura et al., U.S. Pat. No. 4,704,362; Hinnen et al., PNAS USA 75:1929–1933, 1978; Murray et al., U.S. Pat. No. 4,801,542; Upshall et al., U.S. Pat. No. 4,766,075; and Sambrook et al., Molecular Cloning: A Laboratory Manual 2nd Ed., Cold Spring Harbor Laboratory Press, 1989, all of which are herein expressly incorporated by reference in their entirety.

Calcium phosphate transfection, DEAE-Dextran mediated transfection, or electroporation are but an example of different methods of introducing the construct into the host cell. (Davis, L., Dibner, M. Battey, I., Basic Methods in Molecular Biology, (1986)). The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., Molecular Cloning: A Laboratory Manual, Second Edition, Cold Spring Harbor, N.Y., (1989).

Transcription of the DNA encoding the polypeptides of the present invention by higher eurkaryotes may be increased by inserting an enhancer sequence into the vector. Enhancers are cis-acting elements of DNA, usually comprising 10 to 300 base pairs that act on a promoter to increase its transcription. Examples of appropriate enhancer sequences include SV40 enhancer, a cytomegalovirus early promoter enhancer, the polyoma enhancer, and adenovirus enhancers.

Recombinant expression vectors will generally include origins of replication and selectable markers which permit the transformation of the host cell. Examples of origins of replication and selectable markers for use with the present invention include the ampicillin resistance gene of *E. coli* and *S. cerevisiae* TRP1 gene and a promoter derived from a highly-expressed gene which directs transcription of a downstream structural sequence. Such promoters can be derived from operons encoding glycolytic enzymes such as 3-phosoglycerate kinase (PGK), α-factor, acid phosphatase, or heat shock proteins. The heterologous structural sequence is assembled in appropriate phase with translation initiation and termination sequences and a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purified of expressed recombinant product.

Useful expression vectors for bacterial use are constructed by inserting one or more structural DNA sequences encoding one or more desired proteins together with suitable translation initiation and termination signals in operable reading phase with a functional promoter. The vector will comprise one or more phenotypic selectable markers and an origin of replication to ensure maintenance of the vector and provide suitable amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice. As a representative but nonlimiting example, useful expression vectors for bacterial use can comprise a selectable marker and bacterial origin of replication derived from commercially available plasmids comprising genetic elements of the well known cloning vector pBR322, (ATCC 37017). These pBR322 "backbone" sections are combined with an appropriate promoter and the structural sequence to be expressed. Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents. These methods are well known to those of ordinary skill in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. As noted elsewhere herein, the α1,2 and α1,3 fucosyltransferases of the present invention may also be incorporated into one or more transgenic mammals.

The α1,2 and α1,3 fucosyltransferases can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography and combinations thereof. It is preferred to have low concentrations (approximately 0.15–5 mM) of calcium ion present during purification. (Price et al., J. Biol. Chem., 244:917 (1969)). Finally, high performance liquid chromatography (HPLC) can be employed for final purification steps.

The polypeptides of the present invention may be naturally purified products, or products of chemical synthetic procedures, or produced by recombinant techniques from a prokaryotic or eukaryotic host (for example, by bacterial, yeast, higher plant, insect and mammalian cells in culture). Polypeptides of the invention may also include an initial methionine amino acid residue.

A recombinant fucosyltransferase of the invention, or functional fragment, derivative or analog thereof, may be expressed chromosomally, after integration of the fucosyltransferase coding sequence by recombination. In this regard any of a number of amplification systems may be used to achieve high levels of stable gene expression (See Sambrook et al., 1989, supra).

The cell into which the recombinant vector comprising the nucleic acid encoding the α1,2 and α1,3 fucosyltransferases is cultured, is any cell culture medium which provides for the expression of fucosyltransferase by the cell under appropriate conditions. If full length fucosyltransferase is expressed it will comprise an integral membrane binding portion. If a fucosyltransferase lacking a membrane binding domain is expressed, it can then be recovered from the culture according to methods well known in the art. Representative examples of such methods are described in detail, infra.

Any of the methods previously described for the insertion of DNA fragments into a cloning vector may be used to construct expression vectors which contain a gene consisting of appropriate transcriptional/translational control signals and the protein coding sequences. These methods may include in vitro recombinant DNA and synthetic techniques as well as in vivo recombination.

The polypeptides, fragments, derivatives, analogs, or cells expressing the polypeptides can be used as an immunogen to produce antibodies thereto. These antibodies can be polyclonal or monoclonal antibodies. The present invention also includes chimeric, single chain, and humanized antibodies, as well as Fab fragments, or the product of a Fab expression library. Various procedures known in the art may be used for the production of such antibodies and fragments. Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96). Techniques described for the production of single chain antibodies (U.S. Pat. No. 4,946,778) can be adapted to produce single chain antibodies to immunogenic polypeptide products of this invention.

The polyclonal or monoclonal antibodies may be labeled with a detectable marker including various enzymes, fluorescent materials, luminescent materials and radioactive materials. Examples of suitable enzymes include horseradish peroxidase, alkaline phosphatase, β-galactosidase, and/or acetylcholinesterase. Examples of suitable fluorescent materials include umbeliferone, fluorescein, fluorescein isothiocyanate, rhodamine, dichlorotriazinylamine fluorescein, dansyl chloride or phycoerythrin. An example of a luminescent material includes luminol. Finally, suitable radioactive materials include $S^{35}$, $Cu_{64}$, $Ga^{67}$, $Zr^{89}$, $Ru^{97}$, $Tc^{99}m$, $Rh^{105}Pd^{109}$, $In^{111}I^{123}$, $I^{125}$, $I^{131}$, $Re^{186}$, $Au^{198}$, $Au^{199}$, $Pb^{203}$, $At^{211}$, $Pb^{212}$ and $Bi^{212}$. The antibodies may also be labeled or conjugated to one partner of a ligand binding pair. Representative examples include avidin-biotin and riboflavin-riboflavin binding protein.

Methods for conjugating or labelling the antibodies with the representative labels may be readily accomplished using conventional techniques such as described in U.S. Pat. No. 4,744,981 (Trichothecene Antibody); U.S. Pat. No. , 5,106,951 (Antibody Conjugate); U.S. Pat. No. 4,018,884 (Fluorengenic Materials and Labelling Techniques); U.S. 20 Pat. No. 4,897,255 (Metal Radionucleotide Labeled Proteins for Diagnosis and Therapy); U.S. Pat. No. 4,988,496 (Metal Radionuclide Chelating Compounds for Improved Chelation Kinetics); Inman, Methods in Enzymology, Vol. 34, Affinity Techniques, Enzyme Purification; Part B, Jacoby and Wichek (eds) Academic Press, New York, P. 30, 1974; and Wilcheck and Bayer, The avidin-Biotin Complex in Bioanalytical Applications Anal. Biochem. 171:1–32, 1988. All of these references are hereby expressly incorporated by reference in their entirety.

Due to the degeneracy of nucleotide coding sequences, other DNA sequences which encode substantially the same amino acid sequence as the C. elegans α1,2 and α1,3 fucosyltransferases genes described herein may be used in the practice of the present invention. These include but are not limited to nucleotide sequences comprising all or portions of fucosyltransferase genes which are altered by the substitution of different codons that encode the same amino acid residue within the sequence, thus producing a silent change. Likewise, the fucosyltransferase derivatives of the invention include, but are not limited to, those containing as a primary amino acid sequence all or part of the amino acid sequence of the fucosyltransferase protein. The fucosyltransferase derivatives may also include altered sequences in which functionally equivalent amino acid residues are substituted for residues resulting in a conservative amino acid substitution. Potential conserved and/or semi-conserved substitutions were described infra. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) aminos acids include aspartic acid and glutamic acid.

The genes encoding derivatives and analogs of the invention can be produced by various methods known in the art. The manipulations which result in their production can occur at the gene or protein level. For example, the cloned gene sequence can be modified by any of numerous strategies known in the art, for example, modifications can be accomplished according to the procedures of Sambrook et al., 1989. The sequence can be cleaved at appropriate sites with restriction endonuclease(s), followed by further enzymatic modification if desired, isolated, and ligation in vitro. During the production of the gene encoding a derivative or analog of fucosyltransferase, care should be taken to ensure that the modified gene remains within the same translational reading frame as the TPST coding sequence, uninterrupted by translation stop signals, in the gene region where the desired activity is encoded.

Within the context of the present invention, the fucosyltransferase may include various structural forms of the primary protein which retain biological activity. For example, the fucosyltransferase polypeptide may be in the form of acidic or basic salts or in neutral form. Additionally, individual amino acid residues may be modified by oxidation or reduction and various substitutions, deletions, or additions may be made to the amino acid or nucleic acid sequences, the result being that the biological activity of the fucosyltransferase is retained. Due to degeneracy of the generic code, there may be considerable variation in nucleotide sequences encoding the same amino acid and one of ordinary skill in the art would appreciate that alterations to SEQ ID NOS:1 and 2 could occur naturally and/or synthetically but yet still encode the α1,2 and α1,3 fucosyltransferases of the present invention. Thus, alterations which occur are intended to be within the scope of the present invention.

Mutations in nucleotide sequences constructed for expression of derivatives must preserve the reading frame phase of the coding sequences. Furthermore, the mutations will not create complementary regions that could hybridize to produce secondary mRNA structures, such as loops or hairpins which could adversely affect translation of the receptor mRNA. Mutations may be introduced at particular loci by synthesizing oligonucleotides containing a mutant sequence, flanked by restriction sites enabling ligation to fragments of the native sequence. Following ligation, the resulting reconstructed sequence encodes a derivative having the desired amino acid insertion, substitution, or deletion.

Alternatively, oligonucleotide-directed site specific mutagenesis procedures may be employed to provide an altered gene having particular codons altered according to the substitution, deletion, or insertion required. Deletions or truncations of the α1,2 and α1,3 fucosyltransferases may also be constructed by utilizing convenient restriction endonuclease sites adjacent to the desire deletion. Subsequent to restriction, overhangs may be filled in, and the DNA religated. Exemplary methods of making the alterations set forth above are disclosed by Sambrook et al.

As noted above, a nucleic acid sequence encoding the α1,2 and α1,3 fucosyltransferases can be mutated in vitro or in vivo to create and/or destroy translation, initiation, and/or termination sequences, or to create variations in coding regions and/or form new restriction endonuclease sites or destroy preexisting ones. Preferably, such mutations enhance the functional activity of the mutated fucosyltransferase gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), and/or the use of TAB® linkers (Pharmacia). In particular, PCR techniques are preferred for site directed mutagenesis (see Higuchi, 1989, "Using PCR to Engineer DNA", in PCR Technology: Principles and Applications for DNA amplification, H. Erlich, ed., Stockton Press, Chapter 6, pp. 61–70).

It is well known in the art that some DNA sequences within a larger stretch of sequence are more important than others in determining functionality. A skilled artisan can test allowable variations in sequence, without expense of undue experimentation, by well-known mutagenic techniques which include, but are not limited to, those discussed by D. Shortle et al. (1981) Ann. Rev. Genet. 15:265; M. Smith (1985) ibid. 19:423; D. Botstein and D. Shortle (1985) Science 229:1193; by linker scanning mutagenesis (S. McKnight and R. Kingsbury (1982) Science 217:316), or by saturation mutagenesis (R. Myers et al. (1986) Science 232:613). Each of these references are herein expressly incorporated by reference in their entirety. These variations may be determined by standard techniques in combination with assay methods to enable those in the art to manipulate and bring into utility the functional units of upstream transcription activating sequence, promoter elements, structural genes, and polyadenylation signals. Using the methods described herein the skilled artisan can without application of undue experimentation test altered sequences within the upstream activator for retention of function. All such shortened or altered functional sequences of the activating element sequences are within the scope of this invention.

The nucleic acid molecule of the invention also permits the identification, isolation, and/or synthesis of nucleotide sequences which may be used as primers to amplify a nucleic acid molecule of the invention. For example, the use of polymerase chain reaction (PCR) is contemplated herein. The primers may be used to amplify the genomic DNA of other species which possess fucosyltransferase activity. The PCR amplified sequences can be then further examined to determine the relationship between the various unknown fucosyltransferase genes. The length and base primers for PCR are selected so that they will hybridize to different strands of the desired sequence and at relative positions along the sequence such that an extension product synthesized from one primer when it is separated from its template can serve as a template for extension of the other primer into a nucleic acid of defined length. Primers which comprise the present invention are oligonucleotides of the C. elegans fucosyltransferases described herein which occur naturally as in purified restriction endonuclease digest or are produced synthetically using techniques known in the art such as for example, phosphotriester and phosphodiesters methods (See Good et al., Nucl. Acid Res 4:2157, 1977) or automated techniques (See for example, Conolly, B. A. Nucleic Acids Res. 15:15(8\7): 3131, 1987). The primers are capable of acting as a point of synthesis initiation when placed under conditions which permit the synthesis of a primer extension product which is complementary to the DNA sequence of the invention—i.e., in the presence of nucleotide substrates, an agent for polymerization such as DNA polymerase and at suitable temperature and pH. The primers are preferably sequences that do not form secondary structures by base pairing with other copies of the primer, and which do not form hair pin configurations. The primer may be single or double-stranded. Double-stranded primers may be treated to separate the strands before use. The primer preferably contains between 7 and 25 nucleotides.

The primers may be labeled with detectable markers which allow for detection of the amplified products. Suitable detectable markers are radioactive markers such as $P^{32}$, $S^{35}, I^{125}$, and $H^3$, luminescent markers such as chemiluminescent markers, preferably luminol, and fluorescent markers, preferably dansyl chloride, fluorcein-5-isothiocyanate, and 4-fluor-7-nitrobenz-2-axa-1,3 diazole, exzyme markers such as horseradish peroxidase, alkaline phosphatase, β-galactosidase, acetylchoilinesterase, or biotin. It will be appreciated that the primers may contain non-complementary sequences provided that a sufficient amount of the primer contains a sequence which is complementary to a nucleic acid molecule of the invention or oligonucleotide sequence thereof. Restriction site linkers, which facilitate cloning and sequencing of the amplified product, may also be incorporated into the primers allowing for digestion of the amplified products with the appropriate restriction enzymes. In one embodiment of the invention, a method of determining the presence of a nucleic acid molecule having a sequence encoding a fucosyltransferase or a predetermined oligonucleotide fragment thereof, is provided. The method comprises the steps of treating the sample with primers which are capable of amplifying the nucleic acid molecule or the predetermined oligonucleotide fragment thereof in a polymerase chain reaction to form amplified sequences, under conditions which permit the formation of amplified sequences, and assaying for amplified sequences in a method well known to those of ordinary skill in the art.

EXAMPLES

1. α1,3 Fucosyltransferase From *C. elegans*

A. Identification of an α1,3 Fucosyltransferase Activity in Total *C. elegans* Homogenates

*Schistosoma mansoni*, a parasitic helminth in animals and humans, is able to synthesize $Le^x$ antigens. Based on this particular activity of *Schistosoma mansoni*, a survey of other helminths for the presence of $Le^x$ determinants was initiated. The results show that $Le^x$-expression is restricted to schistosomes. Fucα1→GlcNAc linkages, however, may be common among all helminths. For example, *D. immitis* and *H. contortus* lack $Le^x$ antigen, but can synthesize Fucα1→GlcNAc linkages. The free-living nematode, *C. elegans*, like most other helminths, lacks expression of either the $Le^x$ or sialyl $Le^x$ antigens.

In order to determine whether *C. elegans* contained α1,3 fucosyltransferases activity, detergent homogenates of adult worms were incubated with the acceptor oligosaccharide LNnT in the presence of $Mn^{2+}$ and the sugar nucleotide donor, GDP-[$^3$H]-Fuc. Analyses of the reaction products demonstrated that extracts of *C. elegans* contain fucosyltransferase activity capable of generating a $^3$H-Fuc-labeled product from LNnT in a manner dependent upon time and the amount of protein in the assay (FIG. 1).

The samples shown in FIG. 1 were prepared as follows. Detergent extracts of adult *C. elegans* were prepared in the presence of protease inhibitors and reacted with 25 μM GDP-$^3$H-Fuc and 5 mM LNnT in 100 mM sodium cacodylate buffer, pH, 7.0 containing 20 mM $MnCl_2$, 15 mM fucose, and 5 mM ATP. Following incubation at 25° C., reactions were applied to columns of QAE-Sephadex and analyzed. FIG. 1 depicts fucosyltransferase activity in *C. elegans* extracts (100 μg) with respect to time. FIG. 1 depicts fucosyltransferase activity in *C. elegans* extracts with respect to protein in a 4 h assay.

Figure 2A:
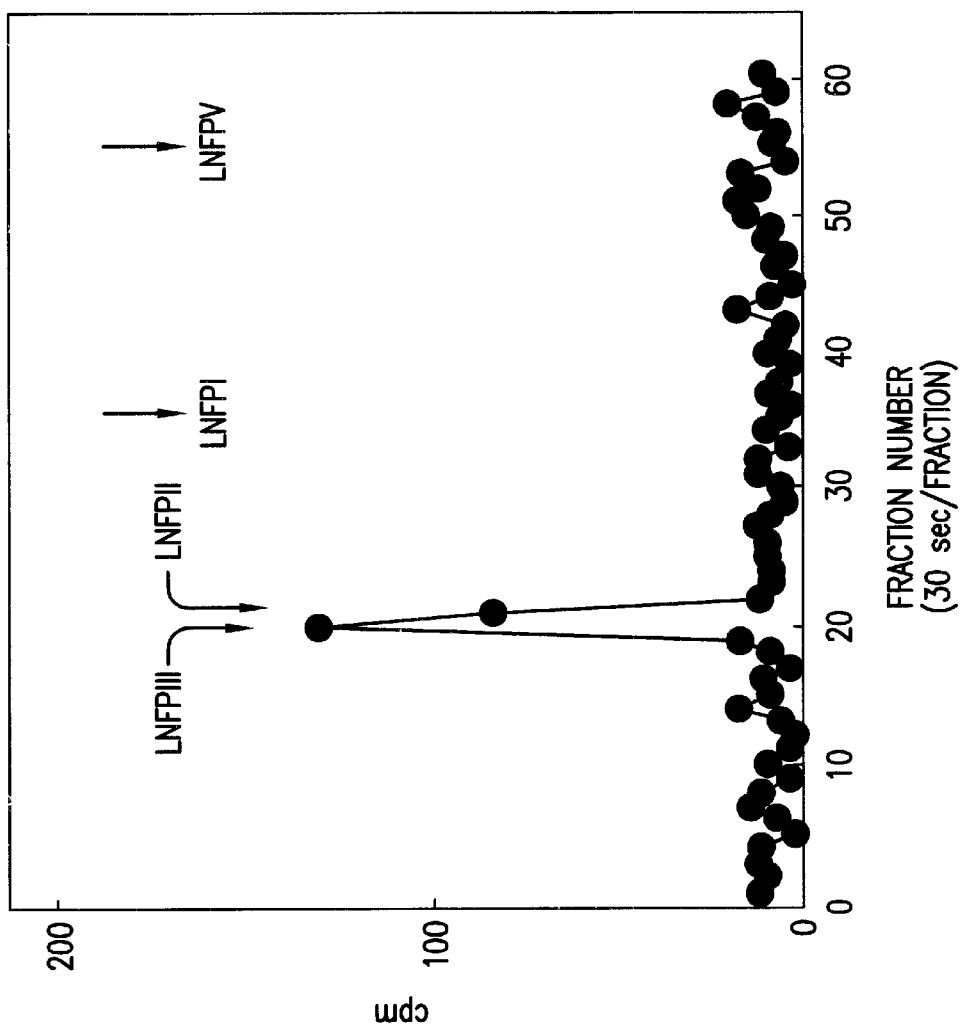
FIGS. 2A–2C graphically depict the characterization of *C. elegans* fucosyltransferase products obtained with the acceptors LNnT and LNT.
Figure 2B:
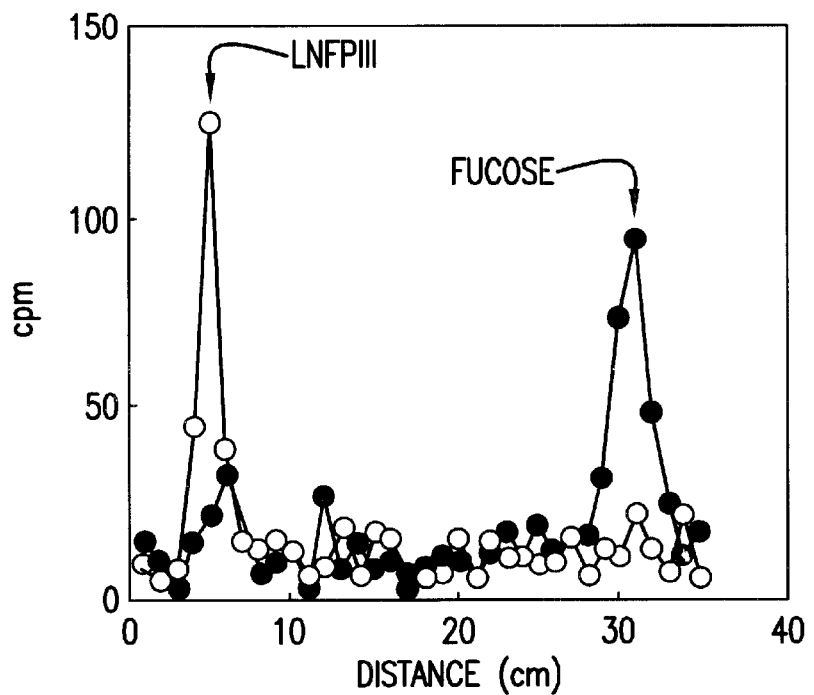
Figure 2C:
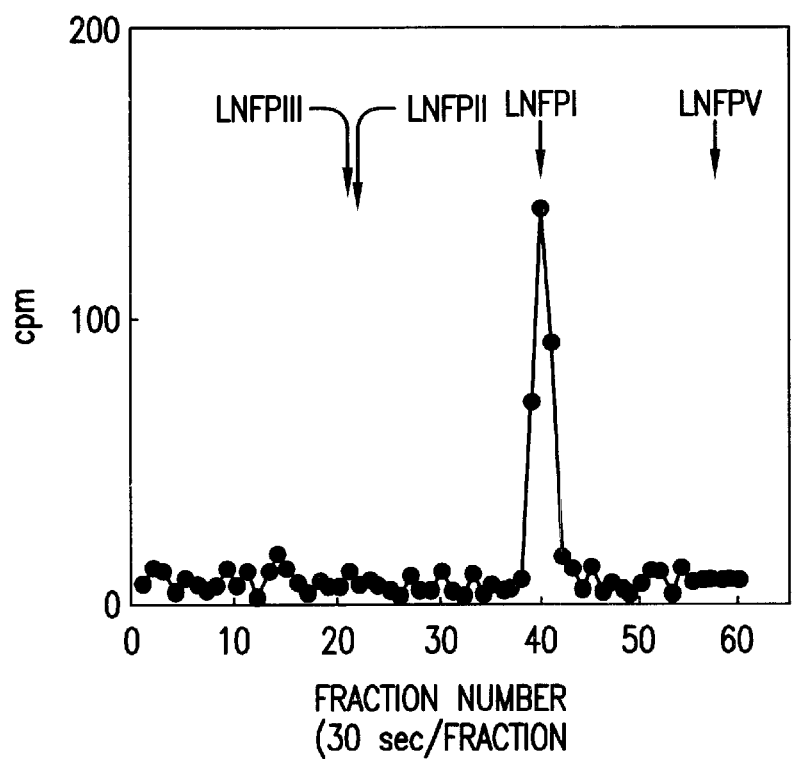

The product was isolated and analyzed by Dionex HPAEC, where it coeluted with standard LNFPIII (FIG. 2A). Treatment of the product with *Streptomyces* α1,3/4 fucosidase, an exoglycosidase specific for Fuc linked α1,3/4 to GlcNAc residues, caused the quantitative release of radiolabeled Fuc (FIG. 2B). FIG. 2A depicts the product of *C. elegans* fucosyltransferase with the acceptor LNnT isolated and analyzed by Dionex HPAEC, as described elsewhere herein. Arrows indicate the elution positions of standards. FIG. 2B depicts the product of *C. elegans* fucosyltransferase with the acceptor LNnT isolated and analyzed by descending paper chromatography before and after treatment with the Streptomyce α1,3/4 fucosidase. Arrows indicate the migration positions of the standard LNFPIII and free fucose. FIG. 2C depicts the product of *C. elegans* fucosyltransferase with the acceptor LNT isolated and analyzed by Dionex HPAEC, as described elsewhere herein. Arrows indicate the elution positions of standards.

The results show that *C. elegans* extracts express an α1,3 fucosyltransferases capable of synthesizing $Le^x$ in vitro using LNnT as the acceptor. These results also show that no other fucosylated product was generated at significant levels by the incubation of LNnT and GDP-[$^3$H]-Fuc, thus precluding the presence of other fucosyltransferases that act on the LNnT acceptor.

Figure 3A:
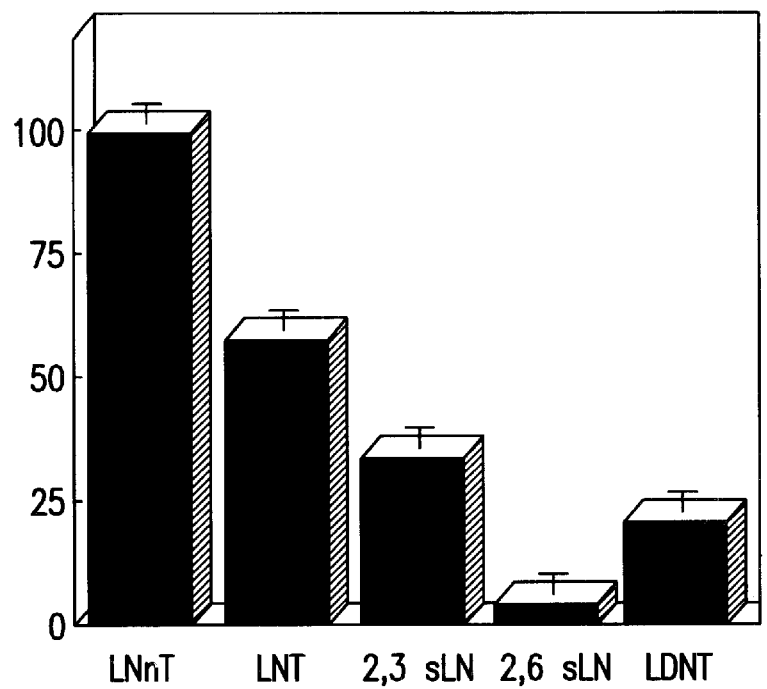
FIGS. 3A–3B graphically depict the acceptor specificity of CEFT-1.

Although α1,3 fucosyltransferases share significant sequence similarities at the amino acid level, each α1,3 fucosyltransferases displays distinct enzymatic characteristics, such as acceptor specificity. To further characterize the α1,3 fucosyltransferases activity in *C. elegans* extracts, α1,3 fucosyltransferases assays were performed with a panel of glycan acceptors. As shown in FIG. 3A, the α1,3 fucosyltransferases activity in *C. elegans* extracts prefers type-2 acceptors (Galβ1→4GlcNAc-R) over type-1 acceptors (Galβ1→3GlcNAc-R).

Figure 3B:
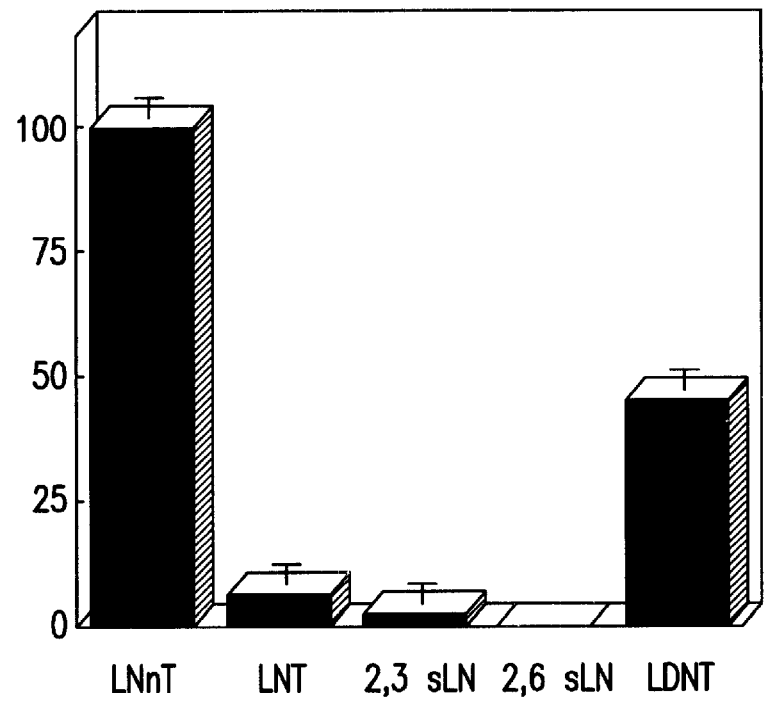

FIG. 3A depicts assays of the α1,3 fucosyltransferases present in *C. elegans* homogenates and FIG. 3B depicts recombinant CEFT-1 expressed in transfected COS7 cells. Fucosyltransferase assays 5 mM of LNnT, LNT, 2,3sLN, 2,6sLN and LDNT as acceptors. The results are expressed as relative activity, where the activity obtained with the acceptor LNnT is taken as 100%. With regard to sialylated acceptors, the 2,3sLN is a suitable acceptor, while no significant amount of Fuc is transferred to 2,6sLN. Overall, the acceptor specificity of the α1,3 fucosyltransferases activity present in *C. elegans* extracts resembles that of human FTIV and the *S. mansoni* α1,3 fucosyltransferases. The *C. elegans* α1,3 fucosyltransferases in extracts utilizes 2,3sLN and LNT more proficiently than does human FTIV.

In order to verify the structures of the reaction products, each product was isolated and analyzed by High pH Anion Exchange Chromatography (HPAEC) on a Dionex system. HPAEC analysis confirmed that the sLe$^x$ trisaccharide was the product obtained with the acceptor 2,3sLN. The product obtained with LNT did not co-elute with standard LNFPII or LNFPV upon Dionex HPAEC analysis (FIG. 2C). Rather the product obtained with the acceptor LNT co-eluted with LNFPI [Fucα1→2]Galβ1→3GlcNAcβ1→3Galβ143 4Glc. These results indicate that, in addition to α1,3 fucosyltransferases activity, *C. elegans* extracts also contain an α1,2 fucosyltransferases activity specific for type-1 chain glycans that does not act on the type-2 acceptor LNnT.

B. Identification of a Fucosyltransferase Gene in *C. elegans* Cosmid K08F8

Members of the emerging α1,3 fucosyltransferases family exhibit a high degree of sequence similarity at the amino acid level. To identify *C. elegans* sequences with possible homologies to known fucosyltransferases, the sequences of human and mouse FTIV were used to perform a TBLASTN search of the *C. elegans* genome data base. This search resulted in the identification of the *C. elegans* cosmid K08F8 (GenBank Accession #Z66497), which harbors a gene with significant sequence similarity to human and mouse FTIV. The product of the putative *C. elegans* α1,3 fucosyltransferases is a 1353 bp cDNA (named CEFT-1) a 451 amino acid polypeptide (SEQ ID NO:1).

Figure 4:
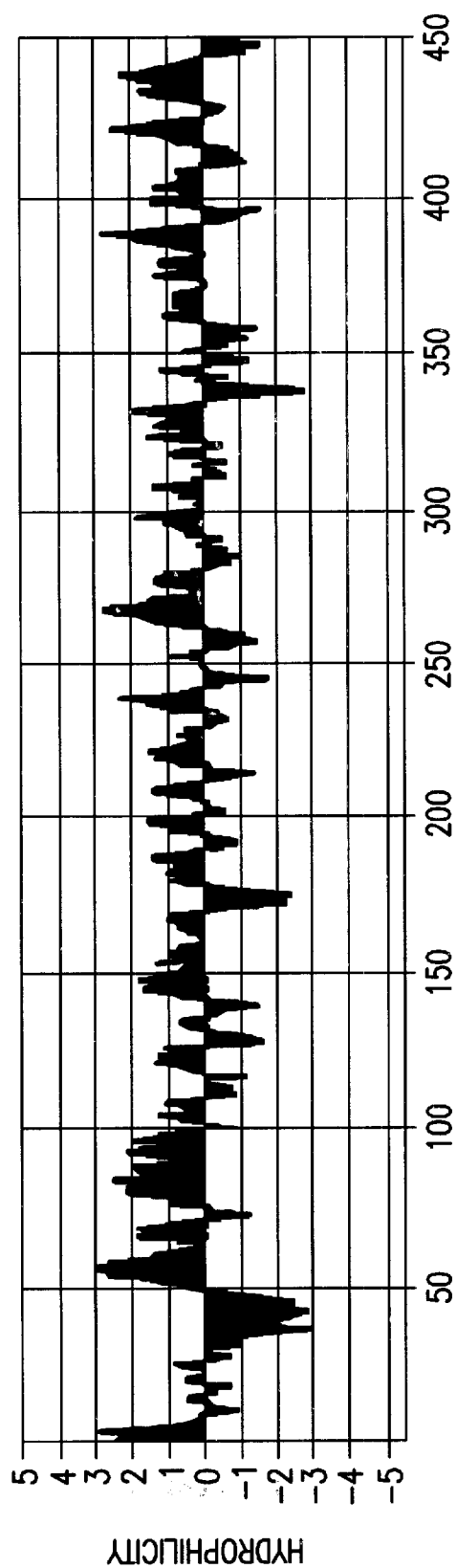
FIG. 4 graphically depicts the hydropathy plot of the amino acid sequence of CEFT-1.

SEQ ID NO:1 depicts the predicted nucleotide and deduced amino acid sequence of the CEFT-1 cDNA. The adenine residue of the putative initiation codon is assigned as 1, while the amino acids encoded by the cDNA are depicted by single letter code. FIG. 4 depicts hydropathy plot of the 451-amino acid polypeptide predicted by the CEFT-1 DNA sequence.

Overall, the CEFT-1 cDNA displays 23% overall identity to human FTIII, chicken FT-1 and bovine fucosyltransferase at the amino acid level. CEFT-1 also displays approximately a 20–23% overall identity to human FTIV, V and VI, although the positions of identity differ between CEFT-1 and these individual enzymes. CEFT-1 displays an overall approximate 50% homology considering conservative substitutions to the sequences of human, chicken, bovine, and mouse fucosyltransferases.

The Kyte-Doolittle hydrophylicity plot of the protein sequence suggests the presence of a 22 amino acid transmembrane domain at the N-terminus (FIG. 4). Thus, the encoded protein displays the typical hallmarks of most Golgi-localized glycosyltransferases, i.e. type II membrane orientation with a relatively small cytosolic -terminus and a large, extracellular, C-terminal region. The present invention contemplates a soluble protein lacking a transmembrane domain and a cDNA encoding said protein. The most conserved region predicted between the CEFT-1 and other α1,3 fucosyltransferases is in the C-terminal domain, indicating that this region is likely to contain the catalytic domain, as seen for other Golgi glycosyltransferases. Interestingly, CEFT-1 contains the conserved motif (YxFxL/VxFENSxxxxYxTEK) found thus far in all α1,3 fucosyltransferases, beginning at Tyr 308 (FIG. 5A).

Figure 5B:
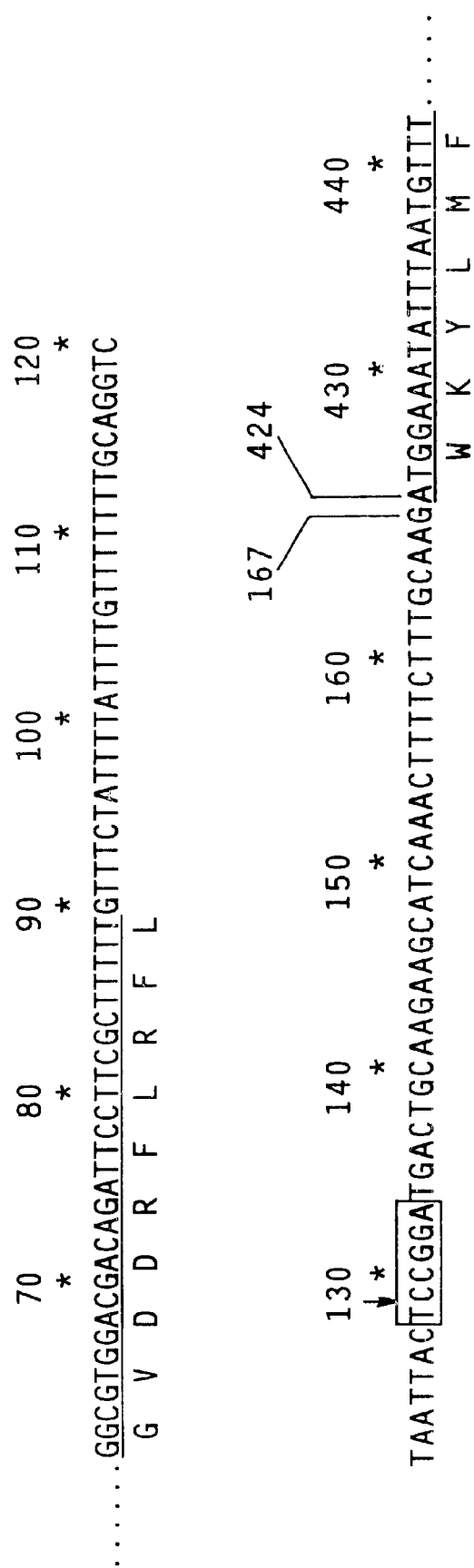

FIG. 5A depicts comparisons shown for human FTIII, bovine FT (bFT), chicken FT-1 (cFT-1) and the *C. elegans* CEFT-1. Amino acid identities are indicated by dark shading and bold letters, while identities between CEFT-1 and other enzymes are indicated by shading alone. The boxed sequences represent the predicted transmembrane domain of the CEFT-1 protein. FIG. 5B depicts the 5' exon/intron sequences of the isolated CEFT-1. A portion of the exon 1 sequence is shown underlined and spans nucleotides 61 through 89. The exon 2 sequence shown is also underlined and begins at nucleotide 424. The partial sequence of intron 1 found in the isolated cDNA spans from nucleotides 90 through 167. The boxed area and the arrow indicate recognition and cleavage site for BspE1.

The GeneBank provided the Expressed Sequence Tags (GenBank Accession #Z66497) for the gene, suggesting its expression in adult worms. Genome sequencing predicts that the CEFT-1 gene contains nine introns dispersed between the ten exons comprising the coding sequence of the enzyme. This is in contrast to FTIII, FTIV, FTV and FTVI, whose entire coding sequence is contained within a single exon; however, the FTVII gene does contain intronic sequences.

C. Cloning of the cDNA Encoding CEFT-1 from *C. elegans*.

Gene-specific primers were designed to amplify the entire coding sequence of the *C. elegans* CEFT-1 from a *C. elegans* cDNA λZAP library. Following amplification, the PCR product was TA-cloned into the mammalian expression vector pCR3.1. A clone was isolated and DNA sequencing confirmed the exon/intron boundaries predicted by the database. The cloned cDNA, however, contained 78 base pairs of the first intron, beginning at nucleotide 90 and ending at nucleotide 167 (FIG. 5B); intron 1 is predicted to be a total of 335 base pairs in size. This partial intron contains an in-frame stop codon beginning at nucleotide 121 and would not be predicted to generate a functional, full-length enzyme. Identification of 5 other clones from the PCR amplification was completed and they also contained this 78 bp partial intron 1.

Therefore, PCR-based mutagenesis was performed to eliminate the 78 base pair sequence and generate a cDNA encoding a continuous ORF. Thus, two cDNAs were obtained for CEFT-1, one is a partial intron-containing clone (+partial intron 1) and the other has a continuous ORF (−partial intron 1). Inspection of the sequence of intron 1 reveals that it contains two potential donor/acceptor splice sites; one pair occurs at the usual 5' and 3' termini of the 335 base pair intron and the other pair occurs 78 pair pairs within intron 1 from the 5' end. The results suggest that this unusual tandem intron is not efficiently spliced and transcripts containing the partial intron 1 accumulate, as described below.

D. Southern and Northern Blot Analysis

Figure 6A:
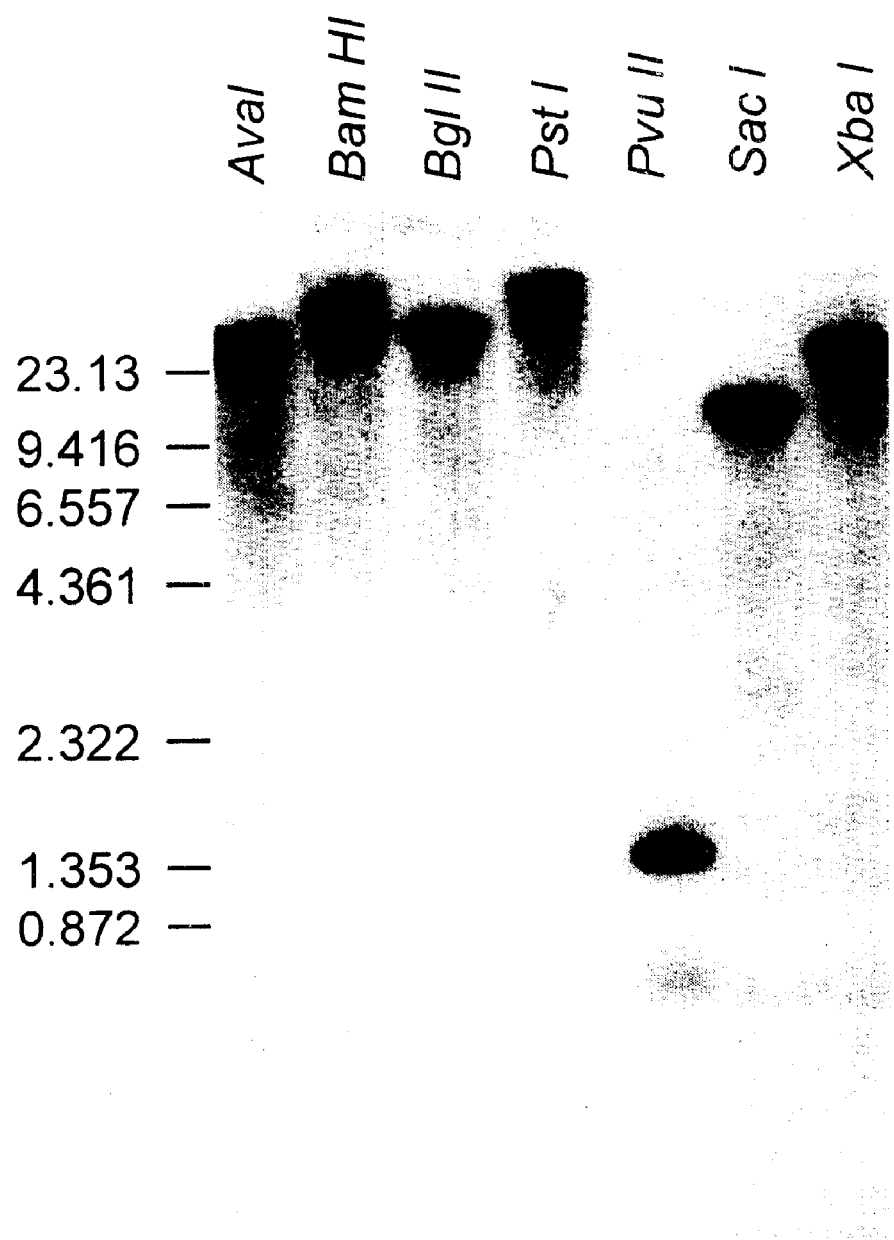
FIGS. 6A–6B graphically depict Southern and Northern blot analysis of *C. elegans* genomic DNA and total RNA.

Mammalian tissues are known to express a wide variety of α1,3 fucosyltransferases in a tissue and/or cell type specific manner. To test the possibility that C. elegans also expresses additional α1,3 fucosyltransferase(s) with sequence similarity to CEFT-1, C. elegans genomic DNA was analyzed by Southern blot, using restriction enzymes that are not predicted to cleave within the introns or exons of the CEFT-1 gene. A single major band was seen for all digests, consistent with the presence of a single copy gene (FIG. 6A). However, a faint additional band was observed in the PvuII and SacI digests (FIG. 6A), suggesting that the C. elegans genome may harbor another gene that is distantly homologous to CEFT-1.

Figure 6B:
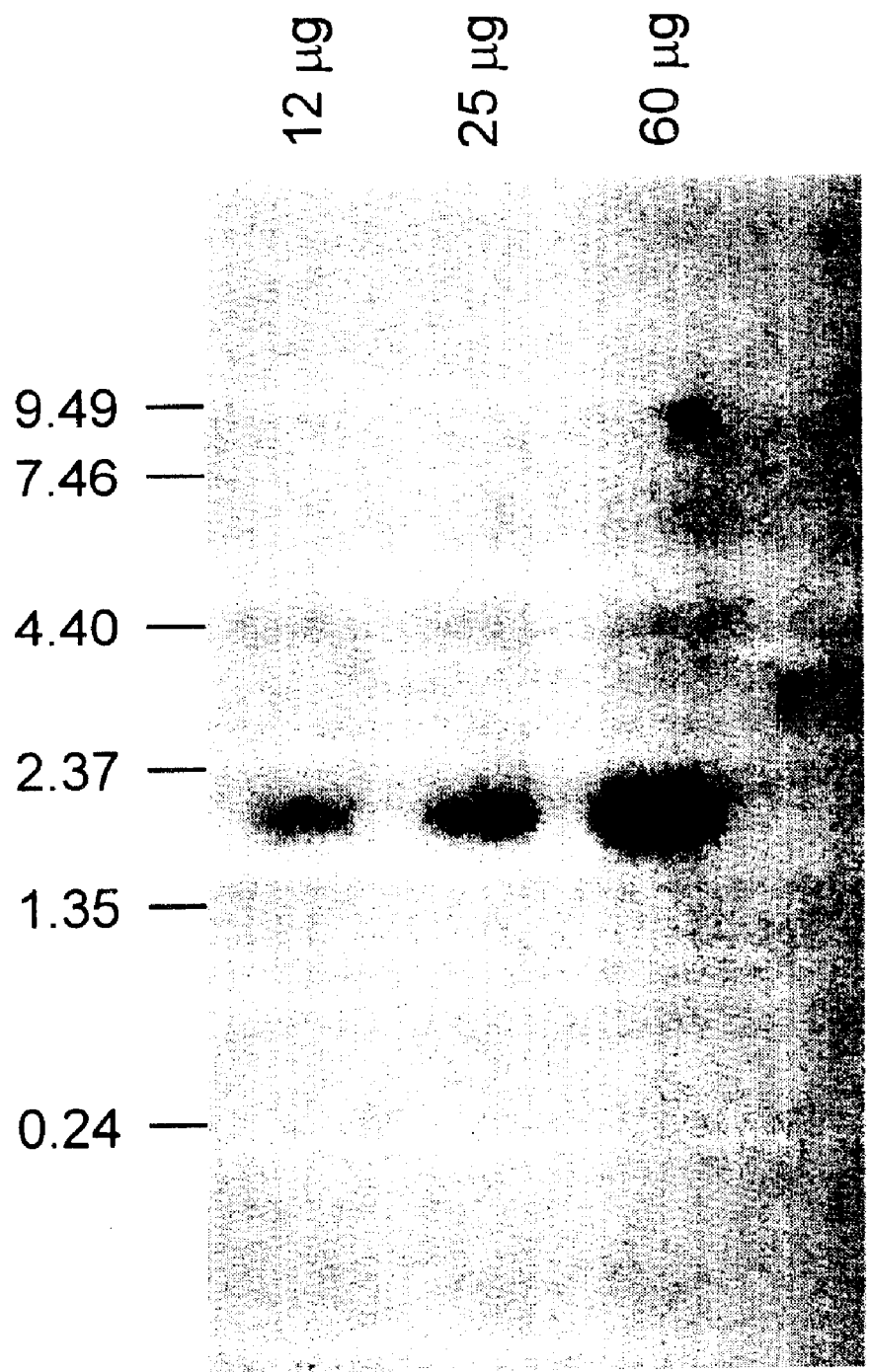

FIG. 6A depicts high molecular weight genomic DNA isolated from C. elegans adults, subjected to restriction enzyme digestion, fractionated on agarose gels, and transferred to nylon membranes. Following pre-hybridization and hybridization with $^{32}$P-labeled CEFT-1 cDNA, blots were washed with high stringency as described in and subjected to autoradiography. Restriction enzymes are indicated. FIG. 6B depicts total RNA from C. elegans adults (12, 25, or 60 µg) was separated on an agarose gel containing formaldehyde, and subsequently transferred to nylon membranes. Hybridization was carried out using isolated CEFT-1 cDNA and the blots were autoradiographed. Size markers in kbp are indicated.

A search of C. elegans genomic sequences in GenBank led to the identification of another gene predicted to encode a protein of 1,652 amino acids, which exhibits some homology to CEFT-1 and mammalian α1,3 fucosyltransferases (Cosmid T05A7, GenBank Accession #U40028). Thus, it is possible that C. elegans contains a number of different α1,3FTs.

In Northern analysis the CEFT-1 cDNA hybridizes to a major 1.9 kb transcript in total C. elegans RNA preparations; faint hybridization was observed to another band at ~4 kb (FIG. 6B). This result is consistent with the RT-PCR experiments described hereinbelow, which confirm expression of CEFT-1 by adult worms.

To determine whether the intron-containing transcript of CEFT-1 (+partial intron 1) with the additional 78 bp intronic sequence exists in adult C. elegans, both RT-PCR analysis and genomic PCR was performed. Primers were designed to produce either a 104 bp product from transcripts that lack the 78 bp partial intronic sequence, or a 182 bp product from those containing the partial intronic sequence. Transcripts containing the complete intron 1 with 335 bp would generate a product containing 438 bp total. All PCR products were treated with the restriction enzyme BspE1, which is predicted to have a cleavage site within the 78 bp partial intronic sequence and at the same position in the 335 bp complete intron 1, but there are no other BspE 1 sites within the gene. Total RNA was isolated and oligo dT-primed cDNA was used as a template to amplify the CEFT-1 cDNA. Control incubations used plasmids containing either the intron-containing clone and a continuous ORF. RT-PCR of the two control plasmids with and without the intronic sequence led to the formation of products corresponding to 182 bp and 104 bp, respectively, as predicted (FIG. 7—lanes 2 and 4).

Figure 7:
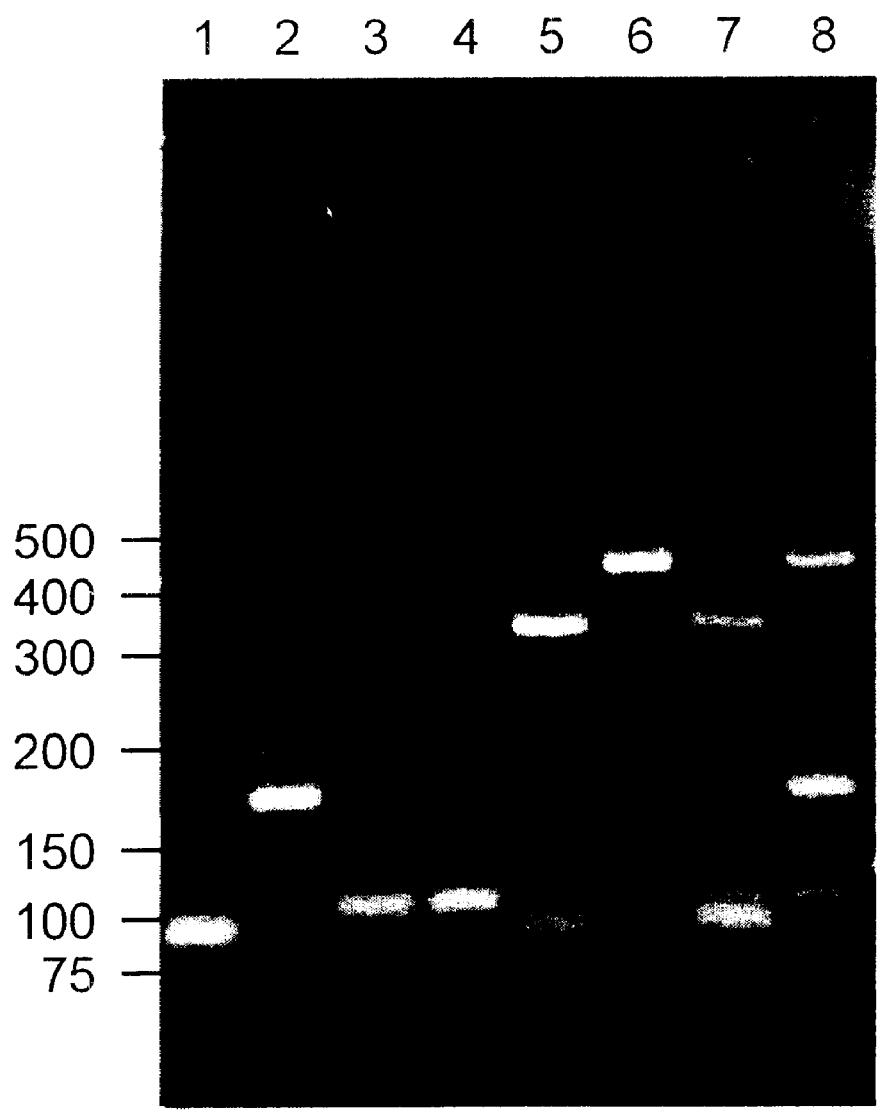
FIG. 7 graphically depicts RT-PCR and genomic PCR of CEFT-1 from adult *C. elegans*.

FIG. 7 depicts total C. elegans RNA used as templates in first strand cDNA synthesis. An aliquot of the cDNA synthesis reaction was used as a template to amplify CEFT-1 coding sequences with primers and conditions (lanes 7 and 8). As controls the cDNAs encoding CEFT-1 (+partial intron 1) (lanes 1 and 2), CEFT-1 (−partial intron 1) (lanes 3 and 4), and C. elegans genomic DNA (lanes 5 and 6) were also amplified. Following amplification, samples were either subjected to treatment with BspEI (lanes 1, 3, 5, and 7) or no treatment (lanes 2, 4, 6, and 8), and subsequently fractionated on a 2% agarose gel containing ethidium bromide and analyzed. Size markers in bp are indicated.

BspE1 treatment caused the degradation of the 182 bp product to generate both a 95 bp and 87 bp product that do not resolve upon electrophoresis (FIG. 7—lane 1), where BspE1 treatment of the 104 bp product was without effect. (FIG. 7—lane 3). RT-PCR of RNA from C. elegans led to the formation of three major bands corresponding in size to 438, 182 and 104 bases pairs (FIG. 7—lane 8). A minor band of ~350 bp with an unknown origin was also observed. Treatment with BspE1 caused a loss of the 438 and 182 bp products, but the 104 bp product was unaffected (FIG. 7—lane 7). Genomic PCR led to the formation of a single major band corresponding to 438 base pairs (FIG. 7—lane 6).

These results indicate that at least three mRNA species for CEFT-1 exist in C. elegans. The major species, represented by the 438 and 182 bp products from RT-PCR, contain a complete intron-1 or the partial 78 bp intronic sequence, respectively. The minor product from RT-PCR with 104 bp represents the fully processed RNA species with an ORF. These results suggest that splicing of mRNA precursors for CEFT-1 is inefficient.

E. Demonstration that CEFT-1 Encodes a Functional α1,3Fucosyltransferases

In order to confirm that the cDNA encoding CEFT-1 corresponds to an α1,3 fucosyltransferases activity, the cDNA encoding CEFT-1 (+/−partial intron 1) was transfected into the African green monkey kidney cell line COS7. COS7 cells do not contain endogenous α1,3 fucosyltransferases activity; however, these cells synthesize the type-1 and -2 oligosaccharide precursors, which are suitable substrates for α1,4 and α1,3 fucosylation, respectively. Transfection of COS7 cells with cDNA encoding CEFT-1 (−partial intron 1) containing a continuous ORF results in about 20-fold level of activity over control cells, using LNnT as the acceptor as shown in Table V.

TABLE V

| Source of cDNA | Product Formation[1] | |
|---|---|---|
|  | (cpm) | (pmol/mg · hr) |
| Mock-transfected | 40 | <7.0 |
| C. elegans CEFT-1 (+ partial intron 1) | 200 | 33.3 |
| C. elegans CEFT-1 | 818 | 140 |

[1]COS7 cells were transfected with cDNAs encoding the C. elegans CEFT-1 (+/− partial intron 1) or were mock transfected with vector alone. Three days post-transfection, cells were assayed for the transient expression of fucosyltransferase activity. Each assay contained 10 mM LNnT, along with 60 µg of CEFT-1-transfected or nontransfected cell extracts, and 50 µM GDP-[$^3$H]-Fuc (25,000 cpm/nmol). Following isolation of neutral products by ion exchange chromatography on QAE-Sephadex columns, radioactivity associated with each experiment was quantified by liquid scintillation counting. The background cpm in the absence of acceptor was subtracted.

When cells were transfected with the cDNA encoding CEFT-1 (+partial intron 1) containing the 78 base pair intronic sequence, significant enzyme activity above control levels was obtained, Table V. This level was about ¼ of that obtained with the cDNA containing a continuous ORF. These results confirm that CEFT-1 encodes a functional α1,2 and α1,3 fucosyltransferases. The lower level of activity obtained with CEFT-1 (+partial intron 1) compared to the cDNA lacking this segment, may reflect the inefficiency of splicing this mRNA in mammalian cells.

In order to confirm the fucosyl linkages in the reaction product generated by CEFT-1, the $^3$H-Fuc-labeled product was isolated and subjected to treatment with the α1,3/4 fucosidase followed by descending paper chromatography. Treatment of the product with the α1,3/4 fucosidase caused quantitative release of $^3$H-fucose from the radiolabeled pentasaccharide product (FIG. 8).

Figure 8:
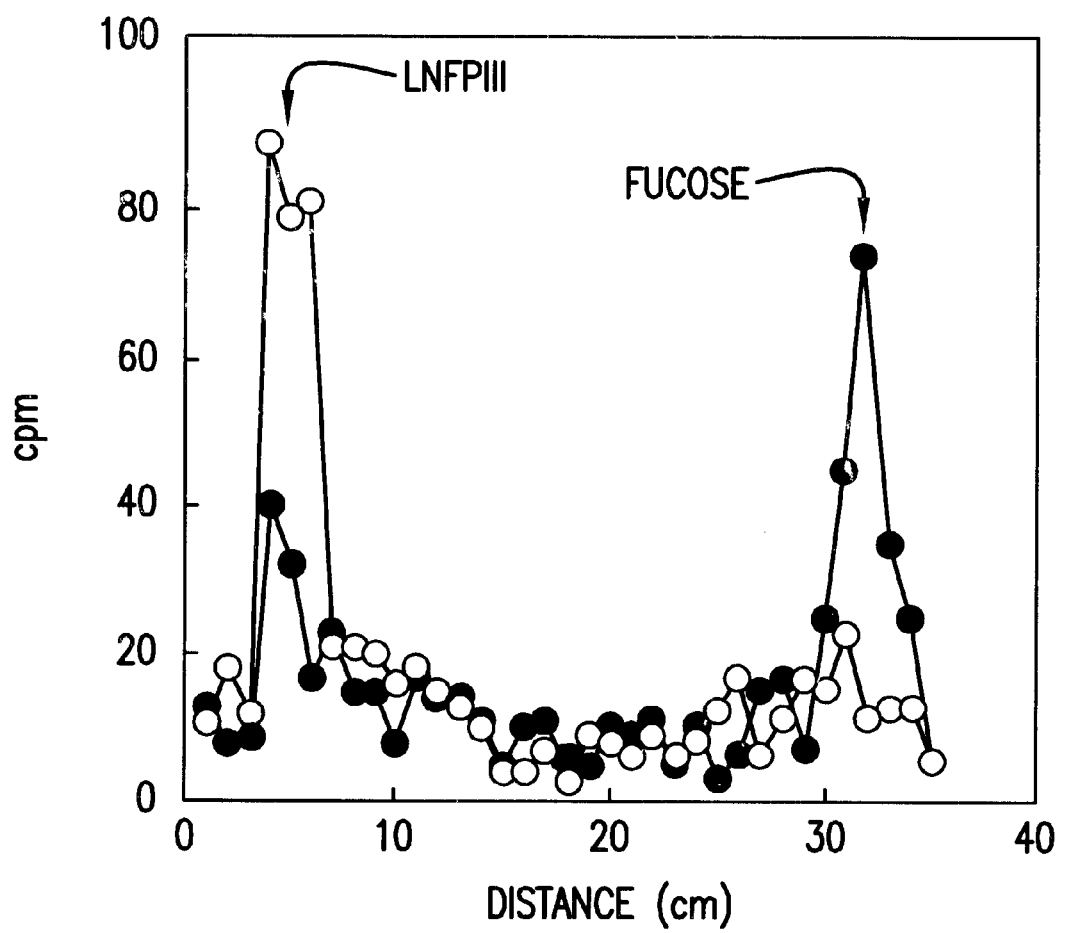
FIG. 8 graphically depicts characterization of the reaction product generated by recombinant CEFT-1.

FIG. 8 depicts the radiolabelled product obtained with COS7 cell extracts transiently expressing CEFT-1 were assayed using LNnT as the acceptor and GDP-[$^3$H]-Fuc as the donor. The isolated product was analyzed by descending paper chromatography before and after treatment with the Streptomyces α1,3/4 fucosidase. Arrows indicated the migration positions of the standard LNFPIII and free fucose.

In control experiments, the non-treated product co-migrates with authentic LNFPIII. These results demonstrate that the CEFT-1 encodes a functional α1,3 fucosyltransferases that can act on a type-2 glycan acceptor to generate the Le$^x$ antigen.

F. Further Characterization of Recombinant CEFT-1

To further characterize the CEFT-1 α1,3 fucosyltransferases activity, the acceptor specificity of the enzyme was assessed. Fucosyltransferase assays were performed using CEFT-1-transfected COS7 cell extract and a variety of oligosaccharide acceptors. The recombinant CEFT-1 has a clear preference for non-sialylated type-2 acceptors over either neutral type-1 acceptors or sialylated type-2 acceptors (FIG. 3B). The poor ability of recombinant CEFT-1 to transfer fucose to the sialylated acceptor is in contrast to the activity observed in adult C. elegans extracts, in which activity toward 2,3sLN was detected (FIG. 3A). These results suggest the possibility that another α1,3 fucosyltransferases may also exist in adult C. elegans that can act on α2,3 sialylated acceptor glycans.

It cannot be ruled out at this time, however, that expression of the enzyme in mammalian cells could adversely affect the acceptor specificity of the enzyme. Since many helminths synthesize the lacdiNAc (LDN) sequence GalNAcβ1→4GlcNAc-R, rather than the typical lactosamine (LN) sequence Galβ1→4GlcNAc-R observed in most vertebrates, we also tested whether the recombinant CEFT-1 can utilize the LDN-based acceptor LDNT GalNAcβ1→4GlcNAcβ1→3Galβ1→4Glc. Incubation of LDNT with GDP-$^3$H-Fuc and extracts from CEFT-1-transfected COS7 cells generated a pentasaccharide product at a level of about 50% of that obtained with the LNnT acceptor. The product generated using the LDNT acceptor was completely sensitive to digestion by the Streptomyces α1,3/4 fucosidase (data not shown), indicating that it has the structure GalNAcβ1→4(Fucα1→3) GlcNAcβ1→3Galβ1→4Glc. These results indicate that the CEFT-1 can act on both LN- and LDN-based acceptors.

The recombinant CEFT-1 in the transfected COS7 cells acts on endogenous glycoproteins. Extracts of CEFT-1-transfected COS7 cells were analyzed by ELISA, using mAb specific for Le$^x$ (CD15) or sLe$^x$ (CSLEX-1) antigens. As controls, we utilized extracts from transfected COS7 cells expressing human FTIV were utilized. Reactivity of CEFT-1-transfected cells with CD15, indicating expression of Le$^x$, as well as FTIV-transfected cells (FIG. 9) was observed.

FIGS. 9A–9C depict extracts of COS7 cells transfected with cDNA encoding (FIG. 9A) human FTIV; (FIG. 9B) CEFT-1; and (FIG. 9C) mock transfected cells were homogenized and with their extracts coated onto microtiter wells at indicated protein concentrations. Following blocking with 1% BSA/PBS, expression of Le$^x$ was monitored by reactivity with CD15. Assays were performed in triplicate and standard deviations are shown by the bars. Data obtained with complete assay components including the primary mAb CD15 and controls in which the primary mAb CD15 was omitted.

The low level of Le$^x$ reactivity in CEFT-1-transfected cells, relative to that in FTIV-transfected cells, is consistent with the observation that FTIV is expressed in COS7 cells at approximately 100 times the level of enzyme activity as CEFT-1. FTIV is unusual among the human α1,3 fucosyltransferases, in that expression of FTIV in COS7 or Chinese hamster ovary cells results in extremely high levels of enzyme activity compared to other human α1,3FTs. Although the reasons for this are unclear, it may result from enhanced stability of the FTIV transcript or higher turnover rates for this enzyme. It should also be noted that the codon preferences for C. elegans differs in several ways from mammalian usage; thus, CEFT-1 may not be efficiently expressed in mammalian cells. No reactivity was observed in ELISA assays performed with monoclonal antibodies against sLe$^x$ or Le$^a$, using either CEFT-1-transfected COS7 cells or FTIV-transfected COS7 cells. These results are consistent with the inability of recombinant CEFT-1 to utilize sialylated acceptor glycans and the known inefficiency with which FTIV utilizes such acceptors.

These results demonstrate that the soil nematode, C. elegans, expresses an α1,3 fucosyltransferases (CEFT-1) capable of acting on both LN-containing acceptor glycans to generate the Le$^x$ antigen, and on LDN-based acceptor glycans to generate α1,3 fucosylated LDN-based structures.

The catalytic activity of recombinant CEFT-1 is highly similar to human FTIV. Both enzymes act predominantly on type-2 rather than type-1 acceptor glycans and neither are efficient with α2,3-sialylated type-2 acceptors. In addition, both enzymes, when expressed in COS7 cells cause formation of the Le$^x$, but not sialyl Le$^x$ antigen.

Although CEFT-1 can generate the Le$^x$ antigen in vitro with appropriate acceptors, we have been unable to detect the presence of Le$^x$ or sialyl Le$^x$ in extracts of total adult *C. elegans*. However, *C. elegans* contains abundant levels of fucosylated glycans reactive with Lotus tetragonolobus agglutinin (LTA). It has been demonstrated that LTA binds with high affinity to non-sialylated glycans containing either terminal Le$^x$ structures or the LDNF-motif GalNAcβ1→4 (Fucα1→3)GlcNAcβ1→R. Preliminary studies also indicate the existence of a β1,4-N-acetylgalactosaminyltransferase (β1,4GalNAcT) in extracts of adult *C. elegans*, like the enzyme in schistosomes, that can synthesize the LDN-based structures. In *H. contortus*, an intestinal parasitic helminth in sheep, expression of a β1,4GalNAcT and an α1,3 fucosyltransferases, similar to CEFT-1 in *C. elegans* was found. *H. contortus* lacks expression of a β1,4GalT capable of synthesizing LN-based structures, however.

Genomic sequencing in *C. elegans* has identified a gene related to mammalian β1,4GalT. Whether the enzyme encoded by this putative β1,4GalT is actually capable of transferring Gal from UDPGal, or utilizes other sugar nucleotide donors, such as UDPGlcNAc, as seen for other members of the β1,4GalT family, remains to be determined. It is conceivable that glycans containing the LN-motif and Le$^x$-based structures are synthesized by *C. elegans*, but other capping reactions or masking may occur that abolish reactivity with anti-Le$^x$ antibodies, as seen, for example, in murine teratocarcinoma cells.

Intron 1 of the CEFT-1 gene has two tandem introns with two pairs of donor/acceptor slice sites. This unusual tandem intron may not be efficiently spliced since the major cDNA identified for CEFT-1 in this study contains 78bp of intron 1. This partial intron would not be expected to allow generation of a functional enzyme, since it contains a stop codon. This partial intron must be a substrate for splicing reactions in vivo, since transfection of COS7 cells with CEFT-1 (+partial intron-1) cDNAs leads to α1,3 fucosyltransferases activity. Enzyme levels are very low, however, relative to that observed for CEFT-1 (-partial intron 1). Although such tandem introns as observed for CEFT-1 are unusual, there is some evidence for unusual intron splicing in other organisms. Several genes of *Euglena gracilis* chloroplasts contain twintrons, i.e. Inters-within-introns, and undergo stepwise splicing reactions leading to functional protein products.

The results shown in FIG. 7 indicate that at least three mRNA species for CEFT-1 exist. The major species contain a complete intron-1 or the partial 78 bp intronic sequence, while completely processed CEFT-1 mRNA represents the minor mRNA species. Based on these observations, the splicing of mRNA precursors for CEFT-1 is inefficient or possibly is regulated in a cell-specific manner. Whether the sequential splicing of CEFT-1 in some manner regulates CEFT-1 expression remains to be determined. Incomplete splicing has been observed for other genes, and is hypothesized to be a major regulatory factor in the expression of those particular genes.

The sequence of CEFT-1 displays a relatively low homology (approximately 23%) to the sequences of vertebrate α1,3 fucosyltransferases, such as human FTIII and bovine FT, but the identity in the predicted catalytic C-terminal domain is significantly higher. CEFT-1 contains the conserved motif identified for several vertebrate and prokaryotic α1,3 fucosyltransferases (*H. pylori*) (YxFxL/IVxFENSxxxxYxTEK) (FIG. 5A). The presence of the motif in the C-terminal catalytic domain suggests that it is involved in interactions with either acceptor glycans or GDP-Fuc.

*C. elegans* homogenates, contain several other fucosyltransferases in addition to an α1,3 fucosyltransferases. We found that extracts as described elsewhere herein contain an α1,2 fucosyltransferase that can generate the H-type antigen LNFPI, using the type-1 acceptor LNT, whereas this α1,2 fucosyltransferase activity does not act on the type-2 acceptor LNnT. Two types of α1,2 fucosyltransferases have been identified in humans, the H-blood group fucosyltransferase and the Secretor fucosyltransferase. Both enzymes transfer Fuc in the α1,2 linkage to terminal Gal residues on both type-1 and -2 backgrounds.

Extracts of *C. elegans* have also been found to contain a fucosyltransferase that acts on an α2,3-sialylated acceptor to generate sialyl Le$^x$, whereas the recombinant form of CEFT-1 acts poorly on such acceptors. This indicates that *C. elegans* contains a second α1,3 fucosyltransferase active in adult extracts. It is also conceivable that the recombinant form of CEFT-1 generated in a mammalian cell line may be adversely affected by such factors as post-translational modifications or lipid-microenvironments, which could alter its activity in vitro. A faint additional band was detected in some digests upon Southern blots, using CEFT-1 as the probe (FIG. 6A), which suggests the possibility of another homologous gene. Genomic sequencing of *C. elegans* has identified another gene predicted to encode a protein of 1,652 amino acids (Cosmid T05A7, Accession #U40028), with significant homology to CEFT-1.

G. Preparation of *C. elegans* Extracts

Frozen *C. elegans* adults were a kind gift of Dr. James B. Rand of the Oklahoma Medical Research Foundation. Worms were suspended in 50 mM cacodylate buffer, pH 7.0, containing 1 tablet/10 ml of Complete Protease Inhibitor Cocktail (Boehringer Mannheim, Indianapolis, Ind.), homogenized on ice with a Biohomogenizer (Model M 133/1281-0; Biospec Products, Inc., Bartlesville, Okla.) using three pulses of 10 sec each, and subsequently subjected to sonication (three pulses of 10 sec each) on a Branson Cell Disrupter (Model 185) to effect complete disruption of the worms. The homogenate was adjusted to 1% Triton X-100 and incubated on ice for 30 minutes to allow solubilization of proteins. The homogenate was centrifuged at 14,000 rpm, at 4° C., for 10 minutes, and the supernatant fraction was collected. Protein concentration of the extract was determined by the BCA protein assay procedure (Pierce Co., Rockford, Ill.). Detergent solubilized extracts were either used directly or stored as aliquots at −80° C. Frozen extracts were thawed only once for use in enzyme assays.

H. Fucosyltransferase Assays

Fucosyltransferase assays were performed in 50 μl of 100 mM sodium cacodylate buffer, pH 7.0, containing 20 mM $MnCl_2$, 5 mM ATP, 15 mM fucose, 25–50 μM GDP-[$^3$H]-Fuc (50–65,000 cpm/nmol) as the sugar-nucleotide donor, 5 mM LNnT, LNT, LDNT, 2,3sLN, or 2,6sLN as acceptors and detergent solubilized extracts of C. elegans adults or CEFT-1- or FTIV-transfected COS7 cells, or parental COS7 cells as the source of fucosyltransferase. Reactions were incubated for different time intervals and terminated by the addition of 450 μl water for reactions containing the neutral acceptors, LNnT, LNT or LDNT, or terminated by addition of 450 μl pyridine/acetate buffer for reactions using either 2,3sLN or 2,6sLN acceptors. C. elegans extracts were assayed at 25° C., but assays with COS7 cell extracts were conducted at 37° C. Neutral products were isolated by ion exchange chromatography on 0.5 ml columns of QAE-Sephadex equilibrated in water.

The columns were washed with deionized water and 0.5 ml fractions were collected. Radioactivity each fraction was determined by liquid scintillation counting. Products of the assays employing 2,3sLN or 2,6sLN were isolated by applying the reaction mixtures to 0.5 ml columns of QAE-Sephadex equilibrated with 2 mM pyridine/acetate buffer, pH 5.5. The columns were washed with 2.5 ml of 2 mM pyridine/acetate to remove, unbound, neutral material. Bound material, containing the charged product, was subsequently eluted from the column by washing with 2.5 ml of 25 mM pyridine/acetate buffer and collecting 0.5 ml fractions. For each enzyme assay, control experiments were performed without added acceptor. Radioactivity obtained in these control assays represented free fucose and was subtracted as background. All assays were performed in duplicate and results reported are an average with an overall standard error of less than 5%.

I. Characterization of Fucosyltransferase Assay Products

Products obtained with LNnT and either extracts of C. elegans or COS7 cells expressing recombinant CEFT were isolated by ion-exchange chromatography and descending paper chromatography. The isolated, radiolabeled products were incubated with 25 μU of Streptomyces α1,3/4 in 25 μl of 50 mM $KH_2PO_4$, pH 6.0, containing 0.1 M NaCl and 0.02% $NaN_3$ for 24 h at 37° C. Following treatment, the samples were analyzed by descending paper chromatography in a solvent system of ethyl acetate:pyridine:acetic acid:water (5:5:1:3). In addition, products obtained with LNT and 2,3sLN were characterized by high-pH anion exchange chromatography (HPAEC) using a Carbopak PA1 column (4×250 mm) on a Dionex instrument. The samples were separated isocratically at 100 mM NaOH for 30 minutes at a flow rate of 1 ml/min. Fractions were collected at 30 second intervals and radioactivity in each fraction was determined by liquid scintillation counting.

J. Cloning and Expression of CEFT-1

The oligonucleotides, 5'-CTCAAAT GCCTTTCCACC-3' (SEQ ID NO:13) and 5'-CAACTAATCTAACGGAATAGAATC-3' (SEQ ID NO:14) were used as forward and reverse primers, respectively, to amplify the CEFT-1 coding sequence from a C. elegans cDNA library in the λZAP vector, kindly provided by Dr. Robert Barstead (Oklahoma Medical Research Foundation, Oklahoma City, Okla.). Reaction mixtures for amplification by Taq DNA polymerase contained 0.2 μM of each primer, 200 μM dNTPs, 2 mM $MgCl_2$, and 5 μl of $10^9$ pfu/ml C. elegans adult cDNA library in a final volume of 100 μl. Amplification was carried out by an initial denaturing step of 94° C. for 5 minutes, followed by 35 cycles of 94° C./1 min, 53° C./1 min, and 72° C./1 min. These cycles were then followed by extension period of 72° C./7 min. Following amplification, an aliquot the about 1.4 kbp product was analyzed on an agarose gel, and the remainder of the product was ligated into the pCR3.1 vector and subsequently transformed into One Shot TOP10F' competent cells according to procedures provided with the Eukaryotic Bidirectional Eucaryotic TA Cloning Kit. Clones containing either sense or antisense inserts were selected, amplified, and maxipreps were prepared using Qiagen kits (QIAGEN, Inc., San Clarita, Calif.). Sequencing of several clones was performed by the Oklahoma State University Recombinant DNA/Protein Resource Facility (Stillwater, Okla.). To determine if the cloned inserts encoded an active α1,3 FT, COS7 cells were transfected with 5 μg of plasmid DNA harboring either CEFT-1 (+/–partial intron 1) (in the plasmid pCR3.1) or FTIV cDNA (in the plasmid pRC/RSV) using Lipofactamine reagent, as described by the manufacturer (GIBCO BRL, Gaithersburg, Md.). Three days post-transfection, cells were harvested solubilized in 50 mM sodium cacodylate buffer containing 1% Triton X-100, and assayed for fucosyltransferase activity as described above.

K. Mutagenesis of CEFT-1 (+Partial Intron 1) cDNA

Mutagenesis of the cloned cDNA encoding CEFT-1 (+partial intron 1) was carried out to eliminate the 78 bp of intron 1. Overlapping fragments of 109 and 1281 bp generated in primary PCR reactions were used as templates in a secondary PCR reaction to generate the intron-free cDNA encoding CEFT-1 (–partial intron 1). The 109 bp fragment was synthesized using 5'-TTACTGACAACATGAAAAAACAAAACACTC-3' SEQ ID NO:15, (forward primer) and 5'-ATATTTCCATAAAAAGCGAAGGAATCTGTC-3' SEQ ID NO:16 (reverse primer). The 1281 bp fragment was generated using 5'-TTCCTTCGCTTTTTATGGA AATATTTAATGTTTGC-3' SEQ ID NO:17, (forward primer) and 5'ACTAATCTAACGGAATAGAA TCTACTAGTGT-3' SEQ ID NO:18, (reverse primer). Using 1 ng of the cloned CEFT-1 (+partial intron 1) cDNA as a template, the two overlapping fragments were generated in reactions containing 2.5 units of Taq DNA Polymerase, 0.250 μM of each primer, 200 μM dNTPs and 3 mM $MgCl_2$ in 100 μl. After an initial denaturing step of 94° C. for 5 minutes, denaturation, annealing, and extension were carried out sequentially at 94° C./1 min, 65° C./1 min, and 72° C./2 min, respectively, for 35 cycles.

Specifically amplified products of 109 and 1281 bp were then isolated from agarose gels and subsequently used as templates in a third PCR reaction. The two overlapping fragments were then incubated in PCR reactions containing 2.5 units of Taq DNA Polymerase, 200 μM dNTPs, and 3 mM $MgCl_2$ to allow the formation of a heteroduplex between the two overlapping fragments. The heteroduplex formed was extended by Taq DNA Polymerase for 1 cycle which included a denaturation step of 94° C. for 1 minute, an annealing step of 62° C./1 min, and an extension period at 72° C./10 min. Following the extension of the heteroduplex into a full-length product, amplification was achieved by including 0.2 μM of the oligonucleotides, 5'-ACAACATGAAAAAACAAAACACTCCTC-3' SEQ ID NO:19, (forward primer) and 5'-CTAATCTAACGGAATAGAATCTACTAG-3' SEQ ID NO:20, (reverse primer). Amplification was carried out using the same program for generating the 109 and 1281 bp produces described above.

L. RT-PCR and Genomic PCR of CEFT-1

The existence of a fully processed cDNA encoding CEFT-1 (−partial intron 1) was demonstrated using RT-PCR in conjunction with restriction enzyme digestion. Oligo-dT primed first strand cDNA was synthesized, utilizing Superscript II reverse transcriptase (GIBCO BRL, Gaithersburg, Md.) under recommended conditions, from 6 μg of total C. elegans RNA, isolated using the RNAgents Total RNA Isolation System (Promega, Madison, Wis.). The first strand cDNA was used as a template in PCR reactions to amplify cDNAs encoding CEFT-1 transcripts using the oligonucleotides, 5'AACCAGTTGTCGTTGGCTC-3' SEQ ID NO:21, (forward primer) and 5'-GAGCATAAATAACAAGAAGATATGTG-3' SEQ ID NO:22, (reverse primer) in reactions containing 10 μM of each primer, 2.5 units of Taq DNA polymerase, 2.5 mM MgCl$_2$, 200 μM dNTPs, and 2 μl of first strand cDNA or 100 ng of C. elegans genomic DNA in a volume of 100 μl. After an initial annealing step of 94° C. for 5 minutes, the reactions were subjected to 35 cycles of 94° C. 1 minute, 60° C. for 1 minute, and 72° C. for 1 minute, followed by a extension at 72° C. for 7 minutes.

In control experiments, the same primer pair was used to amplify the cDNAs encoding CEFT-1 (+/−partial intron 1) from 1 ng of the plasmids harboring each of the inserts, using identical conditions described. Following PCR amplifications, amplified fragments were concentrated by precipitation and subsequently treated with 20 U of the restriction enzyme BspEI for 1 h at 37° C. Following enzyme digestion, reactions were fractionated on a 2% agarose gel containing 10 μg/ml ethidium bromide.

M. ELISA

Cell extracts from COS7 cells transfected with CEFT-1 (+/−partial intron 1) and FTIV cDNAs and non-transfected cells were diluted in PBS at various concentrations, and absorbed onto wells of microtiter plates for 2 h at room temperature. Following coating, wells were blocked with a 5% BSA/PBS solution and were washed 5× in PBS/0.3% TWEEN-20 solution. Monoclonal antibodies reactive with Le$^x$, Lea, and sLe$^x$ determinants were incubated with coated wells for 1 h at room temperature. After a 5× washing step, bound primary antibodies were detected using horseradish peroxidase-conjugated goat anti-mouse IgM antibodies. Following addition of substrate, absorbance was read at 405 nm.

N. Southern and Northern blots

High molecular weight C. elegans genomic DNA was prepared from adult worms using procedures previously described (at Website htpp://eatworms.swmed.edu). Genomic DNA (10 μg) was digested with restriction endonucleases, fractionated through a 0.9% agarose gel, and subjected to Southern blot analysis. Briefly, restricted DNA was transferred to nylon membranes and cross-linked by UV irradiation. Blots were prehybridized in Rapid Hyb hybridization buffer (Amersham Life Science) according to the manufacturer's procedures and subsequently hybridized in the same buffer containing CEFT-1 (+partial intron 1) cDNA radiolabelled with $^{32}$P-dCTP by random priming (Pharmacia Biotech). After a 2h hybridization period, blots were subjected to two 15-minute low stringency washes (2×SSC, 0.1% SDS) at room temperature, followed by a 30 minute, high stringency wash at 65° C. in 0.1×SSC, 0.1% SDS. The blots were then subjected to autoradiography.

For Northern blots, total RNA was prepared from C. elegans adults using the Total RNA isolation kit (Promega). RNA samples were electrophoresed through a 1.2% agarose gel containing formaldehyde and transferred to a nylon membrane. Northern blots were prehybridized in Rapid Hyb buffer as described by the manufacturer's procedures, and probed with the radiolabelled CEFT-1 (+partial intron 1) cDNA probe. Following hybridization, blots were rinsed twice at room temperature with 2×SSC, 0.1% SDS and stringently washed at 65° C. with 0.1% SSC, 0.1% SDS. The blots were then exposed to film and processed.

2. α1,2 Fucosyltransferase from C. elegans

As stated above, the C. elegans nematode also demonstrated α1,2 fucosyltransferase activity. The α1,2 fucosyltransferase was isolated and purified according to the procedures outlined above with respect to the α1,3 fucosyltransferase.

A. Expression Enzyme Activity by Recombinant Enzyme in 293T Cells

The plasmid DNA (PcDNA4/HisMax) harboring the cDNA encoding C. elegans α1,2-fucosyltransferase was transfected into 293T cells using FuGENE6 transfection reagent. Three days posttransfection, cells were harvested, solubilized in 50 mM sodium cacodylate buffer containing 1% Triton X-100, and assayed for fucosyltransferase activity. COS7 cells was primarily selected for transfection, but transfection resulted in obvious toxicity to COS7 cells, especially after two days posttransfection.

Figure 10:
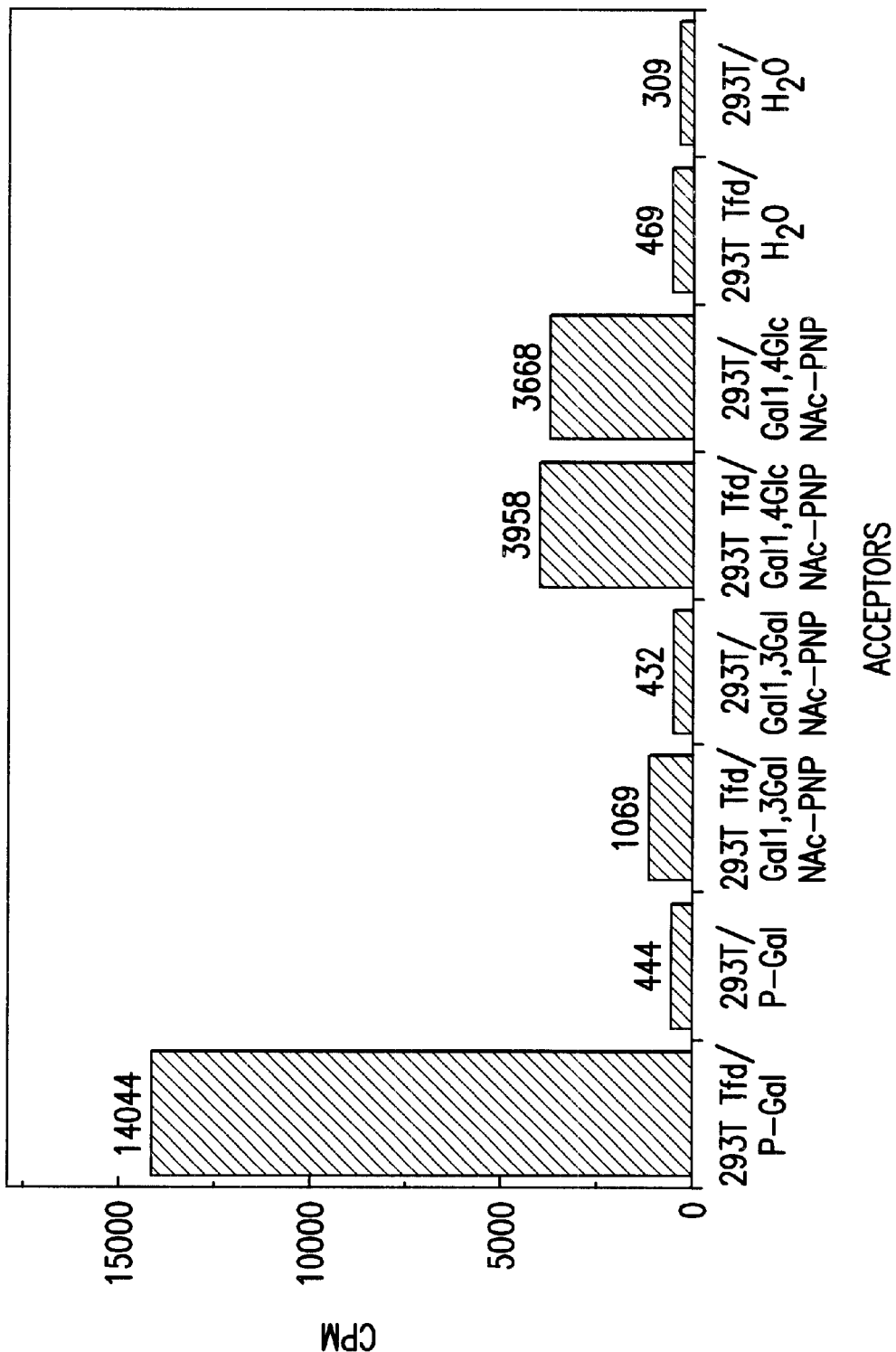
FIG. 10 graphically depicts α1,2-fucosyltransferase activity in transfected and untransfected 293T cells.

The product of the recombinant C. elegans α1,2-fucosyltransferase in 293T cells with the acceptor Gal-phenyl was isolated by Sep-Pak vac 3cc (C18 cartridges) column. Treatment of the product with α1,2-fucosidase, an exoglycosidase specific for Fuc linked α1,2 to Gal residues caused the quantitative release of radiolabeled Fucose. These results verify that recombinant C. elegans α1,2-fucosyltransferase in 293T cells express an α1,2-fucosyltransferase activity.

α1,2-fucosyltransferase activity in transfected and untransfected 293T cells is shown in FIG. 10. Detergent extracts of transfected and untransfected 293T cells were prepared in the presence of protease inhibitors and reacted with 25 μM GDP-$^3$H-fucose and 5 μM acceptors in 100 μM sodium cacodylate buffer, ph7-0 containing 20 μM MnCl$_2$, 15 μM fucose, and 5 μM ATP. Following incubation at 37° C. for 6 hours, reactions were applied to columns of Sep.Pak Vac 3cfc (C18 cartridges) and eluted with 1-butanol. The radioactivity was determined by liquid scintillation counting.

The deduced amino acid and nucleotide sequence of the C. elegans α1,2 fucosyltransferase is shown in SEQ ID NO:2.

The present invention discloses that (1) a relatively primitive soil dwelling nematode, Caenorhabditis elegans, synthesizes glycoconjugates containing α-fucosylated residues; (2) contains the enzymes or α-fucosyltransferases responsible for their synthesis; and (3) contains genes and mRNA encoding the production of these enzymes. In particular an α1,3-fucosyltransferase (α1,3-Fuc-T) has been identified that can synthesize the Fucα1→3GlcNAc-R linkage, an α1,4-fucosyltransferase (α1,4-Fuc-T) that can synthesize the Fucα1→4GlcNAc-R linkage and an α1,2-fucosyltransferase (α1,2-Fuc-T) that can synthesize the Fucα1,2Gal-R linkage. The Fucα1→3GlcNAc-R linkage is found in the human Lewis x antigen Galβ1→4(Fucα1→3)GlcNAc-R, the sialyl Lewis x antigen NeuAcα2→3Galβ1→4(Fucα1→3)GlcNAc-R and the fucosylated lacdiNAc antigen GalNAcβ1→4(Fucα1→3)GlcNAc-R. The Fucα1→4GlcNAc-R linkage is found in the human Lewis a antigen Galβ1→3(Fucα1→4)GlcNAc-R, the sialyl Lewis a antigen NeuAcα2→3Galβ1→3(Fucα1→4)GlcNAc-R, and the Lewis y antigen Fucα1→2Galβ1→3(Fucα1→4)GlcNAc-R. The Fucα1→2Gal-R linkage is found in the human O(H) antigen of the classic ABO(H) blood group.

The cDNA encoding the α1,3-Fuc-T is disclosed in this invention. In addition, a method of using the mature recombinant forms of the α1,3-Fuc-T, α1,4-Fuc-T and α1,2Fuc-T to synthesize glycoconjugates is disclosed in this invention. The cDNA sequence of the α1,3 -Fuc-T bears little identity to possible homologous genes in higher animals. In addition, the C. elegans α1,3-Fuc-T and α1,4-Fuc-T and α1,2-Fuc-T enzyme activities have novel and unexpected activities significantly different from their counterparts in higher animals and humans. These C. elegans enzymes can be used in vitro and in vivo to produce synthetic oligosaccharides and other glycoconjugates known to have biological activities in higher animals and humans.

It will be appreciated that the invention includes nucleotide or amino acid sequences which have substantial sequence homology with the nucleotide and amino acid sequences of the α-1,3 and α-1,2 fucosyltransferases and genes thereof described herein. The term "sequences having substantial sequence homology" means those nucleotide and amino acid sequences which have slight or inconsequential sequence variations from the sequences described herein, i.e. the homologous sequences function in substantially the same manner to produce substantially the same polypeptides as the actual sequences. The variations may be attributable to local mutations or structural modifications. Substantially homologous sequences further include sequences having at least 50% sequence homology with the C. elegans α-1,3 or α-1,2 fucosyltransferase polynucleotide or polypeptide sequences shown herein or other percentages as defined elsewhere herein.

The invention further contemplates polynucleotides which are at least about 50% homologous, 60% homologous, 70% homologous, 80% homologous or 90% homologous to the coding sequences of SEQ ID NO:1 and/or SEQ ID NO:2 where homology is defined as strict base identity, wherein said polynucleotides encode proteins having fucosyltransferase activity.

The present invention further contemplates nucleic acid sequences which differ in the codon sequence from the nucleic acids defined herein due to the degeneracy of the genetic code, which allows different nucleic acid sequences to code for the same protein as is further explained herein above and as is well known in the art. The polynucleotides contemplated herein may be DNA or RNA. The invention further comprises DNA or RNA nucleic acid sequences which are complementary to the sequences described above.

The present invention further comprises polypeptides which are encoded by the polynucleotide sequences described above, including versions which lack the transmembrane domain and which are therefore soluble.

The present invention further contemplates polypeptides which differ in amino acid sequence from the polypeptides defined herein by substitution with functionally equivalent amino acids, resulting in what are known in the art as conservative substitutions, as discussed above herein.

Also included in the invention are isolated DNA sequences which hybridize to the DNAs set forth herein or described herein under stringent (e.g., 4×SSC at 65° C. or 50% formamide and 4×SSC at 42° C.), or relaxed (4×SSC at 50° C. or 30–40% formamide at 42° C.) conditions and which have fucosyltransferases activity.

Thus, it should be apparent that there has been provided in accordance with the present invention α-1,3 and α-1,2 fucosyltransferases from C. elegans and transgenic mammals incorporating same that fully satisfy the objectives and advantages set forth above. Although the invention has been described in conjunction with specific embodiments thereof, it is evident that many alternatives, modifications, and variations will be apparent to those skilled in the art given the present specification and claims. Accordingly, it is intended to embrace all such alternatives, modifications, and variations that fall within the spirit and broad scope of the appended claims.

SEQUENCE LISTING

<160> NUMBER OF SEQ ID NOS: 22

<210> SEQ ID NO 1
<211> LENGTH: 1353
<212> TYPE: DNA
<213> ORGANISM: Caenorhabditis elegans

<400> SEQUENCE: 1
atgaaaaaac aaaacactcc tcgtgttttc ggttactatg caaccagttg tcgttggctc    60

```
ggcgtggacg acagattcct tcgctttta tggaaatatt taatgtttgc ttgttgtatc    120
acatatcttc ttgttatta tgctccaatt tcaaaatctg aacaaaagga ttggaaagaa    180
ggcgaaatag agcttagcaa tgatcatgaa ttagatgttc caattcttca aaagaagaa     240 ttgaagccac aacaacgacc gtcatttgaa gaaaatgtac ccaaaaagaa gactttaat    300 tttaatccag ttgaaaagga accatttgat gtggaagaag tgctcacatc aagtgatatt    360
aaattagaag aacgaatgac cgcaactgta atacctggac aaaagcgatt aatcctgtca    420
tggaacgccg gtcattctca agataatctt caaggatgcc ctgattggaa ttgtgaattc    480
acgcaagtcc gtgcaagggc tccagatgca gatgctgttc ttattgctca tatggacaat    540
gattttgtcc cgaagcctaa tcaatatgta gtgtatttca gccaggagtc accagctaat    600
tctggaattc aaattccaag gcctgattat atcaacatga cactgggatt tcggcacgat    660
acacctgctg gttctcctta tggatacact gttaaattgg gcgccaagtc ccgaaaaact    720
ggacaagttg tggatgccaa tttagtcaat ggaaaagcaa aaggagctgc ttggtttgtg    780
agccattgtc agacaaacag caagagagaa gattttgtta aaaaactaca gaaacatttg    840
caaattgaca tttacggtgg ttgtggtcca atgaaatgtg cacgtggaga cagcaaatgt    900
gacacgatgc tggataccga ttatcatttc tatgtcacat ttgaaaattc aatttgcgaa    960
gattatgtga ctgaaaaact tggaaatcg ggatatcaaa atactattat tccattggtg    1020
ttaaagagaa agcttgtcga gccttttgta ccaccaaaca gcttcattgc tattgacgat    1080
tttaaaagtg tgaaagaaat gggagactat ctcaattatt taatgaataa taagaccgcc    1140
tacatggaat acttcgaatg gaggcacgac tacaaagttg tatttcttga tgggtctcac    1200
cacgatgttc ttgagagacc gtggggcttc tgtcaagttt gtcgaatggc ttggacggag    1260
ccacggcaga aggttttaat tccgaattgg gatgcgtatt ggcggcaaac atgtgaaaaa    1320
gatggaacac tagtagattc tattccgtta gat                                1353
```

<210> SEQ ID NO 2
<211> LENGTH: 1068
<212> TYPE: DNA
<213> ORGANISM: Caenorhabditis elegans

<400> SEQUENCE: 2

```
atgagaaatg tgaaaggact ttttagctac atgacaaaaa ctaaaagttt ttatatatca     60
ataatagtta taatattcat aatttcatt gttaatagga tgggcccacg caattataat    120
tacaaacaga ttggcacaga aattaactgt gttaagcaca agttgatga acaaagatat    180 ttattatttc ctatgatcac aatactctac aaatatggtt taggaaatca actattcgaa    240
gtattttcac tgcttggcag tgcgcagacc ctcaatcgaa ctgcaatttt caatgctgat    300
gatgatattc ttcaatcaaa gttagattta cttcaaaaac aagtacccca ggttgctgca    360
cgaataattt ccattccaat tgagatagct gaatccactc gatatttatt cctaccagca    420
tgttgtcatt atcaatttcc gtctcttttt cttgtgaac ggagtaaatt tcttgtcatt    480
gatggtcaat attttcagag tttcaaatac ttttcagcaa tagattctct aataagaaaa    540
ttgttgaaac cgccgataga cgaagagatt atactaaaaa agatgatcgg aagaaaggat    600
gagttaagat tcaaaaactg cgttcacatt cgtcgtggag attatgtcaa tgattttgac    660
cacgccgaaa cttcctcata ctttacgatt cgagcgattg actacgtaca tacttttgcat    720 cctggcttag tatatctaat aagtgatgat ccaaaatggg ttcggaagca aatagctgaa    780
```

-continued

```
catcttgact atcatgatga tgttaaaatt atggaaacac caataaatgc agcaataaga    840
gatttatatt tttcacaagc tcattgtgat tccgttttga tcactgctcc atcgtcaacg    900
tttggttggt ggattggata catgtccaaa aatcagtcaa atgtttatta ccgagatatt    960
caagaaactg atgatatggt caaatataaa atggtggagg aagacttctt cccgcccacg   1020
tggaaaaagt tgggaatgtc acgaaacggg tcgataattt caaaatag               1068
```

<210> SEQ ID NO 3
<211> LENGTH: 451
<212> TYPE: PRT
<213> ORGANISM: Caenorhabditis elegans

<400> SEQUENCE: 3

```
Met Lys Lys Gln Asn Thr Pro Arg Val Phe Gly Tyr Tyr Ala Thr Ser
 1               5                  10                  15

Cys Arg Trp Leu Gly Val Asp Asp Arg Phe Leu Arg Phe Leu Trp Lys
            20                  25                  30

Tyr Leu Met Phe Ala Cys Cys Ile Thr Tyr Leu Leu Val Ile Tyr Ala
        35                  40                  45

Pro Ile Ser Lys Ser Glu Gln Lys Asp Trp Lys Glu Gly Glu Ile Glu
    50                  55                  60

Leu Ser Asn Asp His Glu Leu Asp Val Pro Ile Leu Gln Lys Glu Glu
65                  70                  75                  80

Leu Lys Pro Gln Gln Arg Pro Ser Phe Glu Glu Asn Val Pro Lys Lys
                85                  90                  95

Lys Thr Phe Asn Phe Asn Pro Val Gly Lys Glu Pro Phe Asp Val Glu
            100                 105                 110

Glu Val Leu Thr Ser Ser Asp Ile Lys Leu Glu Glu Arg Met Thr Ala
        115                 120                 125

Thr Val Ile Pro Gly Gln Lys Arg Leu Ile Leu Ser Trp Asn Ala Gly
    130                 135                 140

His Ser Gln Asp Asn Leu Gln Gly Cys Pro Asp Trp Asn Cys Glu Phe
145                 150                 155                 160

Thr Gln Val Arg Ala Arg Ala Pro Asp Ala Asp Ala Val Leu Ile Ala
                165                 170                 175

His Met Asp Asn Asp Phe Val Pro Lys Pro Asn Gln Tyr Val Val Tyr
            180                 185                 190

Phe Ser Gln Glu Ser Pro Ala Asn Ser Gly Ile Gln Ile Pro Arg Pro
        195                 200                 205

Asp Tyr Ile Asn Met Thr Leu Gly Phe Arg His Asp Thr Pro Ala Gly
    210                 215                 220

Ser Pro Tyr Gly Tyr Thr Val Lys Leu Gly Ala Lys Ser Arg Lys Thr
225                 230                 235                 240

Gly Gln Val Val Asp Ala Asn Leu Val Asn Gly Lys Ala Lys Gly Ala
                245                 250                 255

Ala Trp Phe Val Ser His Cys Gln Thr Asn Ser Lys Arg Glu Asp Phe
            260                 265                 270

Val Lys Lys Leu Gln Lys His Leu Gln Ile Asp Ile Tyr Gly Gly Cys
        275                 280                 285

Gly Pro Met Lys Cys Ala Arg Gly Asp Ser Lys Cys Asp Thr Met Leu
    290                 295                 300

Asp Thr Asp Tyr His Phe Tyr Val Thr Phe Glu Asn Ser Ile Cys Glu
305                 310                 315                 320

Asp Tyr Val Thr Glu Lys Leu Trp Lys Ser Gly Tyr Gln Asn Thr Ile
```

```
              325                 330                 335
Ile Pro Leu Val Leu Lys Arg Lys Leu Val Glu Pro Phe Val Pro Pro
            340                 345                 350
Asn Ser Phe Ile Ala Ile Asp Asp Phe Lys Ser Val Lys Glu Met Gly
        355                 360                 365
Asp Tyr Leu Asn Tyr Leu Met Asn Asn Lys Thr Ala Tyr Met Glu Tyr
    370                 375                 380
Phe Glu Trp Arg His Asp Tyr Lys Val Val Phe Leu Asp Gly Ser His
385                 390                 395                 400
His Asp Val Leu Glu Arg Pro Trp Gly Phe Cys Gln Val Cys Arg Met
                405                 410                 415
Ala Trp Thr Glu Pro Arg Gln Lys Val Leu Ile Pro Asn Trp Asp Ala
            420                 425                 430
Tyr Trp Arg Gln Thr Cys Glu Lys Asp Gly Thr Leu Val Asp Ser Ile
        435                 440                 445
Pro Leu Asp
    450

<210> SEQ ID NO 4
<211> LENGTH: 1068
<212> TYPE: DNA
<213> ORGANISM: Caenorhabditis elegans

<400> SEQUENCE: 4
tactctttac actttcctga aaatcgatg tactgttttt gattttcaaa aatatatagt      60
tattatcaat attataagta ttaaaagtaa caattatcct acccgggtgc gttaatatta    120
atgtttgtct aaccgtgtct ttaattgaca caattcgtgt ttcaactact tgtttctata    180
aataataaag gatactagtg ttatgagatg tttataccaa atcctttagt tgataagctt    240
cataaaagtg acgaaccgtc acgcgtctgg gagttagctt gacgttaaaa gttacgacta    300
ctactataag aagttagttt caatctaaat gaagttttttg ttcatggggt ccaacgacgt    360
gcttattaaa ggtaaggtta actctatcga cttaggtgag ctataaataa ggatggtcgt    420
acaacagtaa tagttaaagg cagagaaaaa agaacacttg cctcatttaa agaacagtaa    480
ctaccagtta taaagtctc aaagtttatg aaaagtcgtt atctaagaga ttattctttt    540
aacaactttg gcggctatct gcttctctaa tatgattttt tctactagcc ttctttccta    600
ctcaattcta agttttttgac gcaagtgtaa gcagcacctc taatacagtt actaaaactg    660
gtgcggcttt gaaggagtat gaaatgctaa gctcgctaac tgatgcatgt atgaaacgta    720
ggaccgaatc atatagatta ttcactacta gttttaccc aagccttcgt ttatcgactt     780
gtagaactga tagtactact acaatttttaa tacctttgtg gttatttacg tcgttattct    840
ctaaatataa aaagtgttcg agtaacacta aggcaaaact agtgacgagg tagcagttgc    900
aaaccaacca cctaacctat gtacaggttt ttagtcagtt tacaaataat ggctctataa    960
gttctttgac tactatacca gtttatattt taccacctcc ttctgaagaa gggcgggtgc   1020
accttttca acccttacag tgctttgccc agctattaaa gttttatc                 1068

<210> SEQ ID NO 5
<211> LENGTH: 355
<212> TYPE: PRT
<213> ORGANISM: Caenorhabditis elegans

<400> SEQUENCE: 5

Met Arg Asn Val Lys Gly Leu Phe Ser Tyr Met Thr Lys Thr Lys Ser
```

```
                 1               5                  10                 15
    Phe Tyr Ile Ser Ile Ile Val Ile Ile Phe Ile Ile Phe Ile Val Asn
                        20                  25                 30

Arg Met Gly Pro Arg Asn Tyr Asn Tyr Lys Gln Ile Gly Thr Glu Ile
                35                  40                 45

Asn Cys Val Lys His Lys Val Asp Glu Gln Arg Tyr Leu Leu Phe Pro
            50                  55                 60

Met Ile Thr Ile Leu Tyr Lys Tyr Gly Leu Gly Asn Gln Leu Phe Glu
    65                  70                  75                     80

Val Phe Ser Leu Leu Gly Ser Ala Gln Thr Leu Asn Arg Thr Ala Ile
                        85                  90                 95

Phe Asn Ala Asp Asp Ile Leu Gln Ser Lys Leu Asp Leu Leu Gln
                    100                 105                110

Lys Gln Val Pro Gln Val Ala Ala Arg Ile Ile Ser Ile Pro Ile Glu
                    115                 120                 125

Ile Ala Glu Ser Thr Arg Tyr Leu Phe Leu Pro Ala Cys Cys His Tyr
            130                 135                 140

Gln Phe Pro Ser Leu Phe Ser Cys Glu Arg Ser Lys Phe Leu Val Ile
    145                 150                 155                    160

Asp Gly Gln Tyr Phe Gln Ser Phe Lys Tyr Phe Ser Ala Ile Asp Ser
                    165                 170                 175

Leu Ile Arg Lys Leu Leu Lys Pro Pro Ile Asp Glu Ile Ile Leu
                180                 185                 190

Lys Lys Met Ile Gly Arg Lys Asp Glu Leu Arg Phe Lys Asn Cys Val
                    195                 200                 205

His Ile Arg Arg Gly Asp Tyr Val Asn Asp Phe Asp His Ala Glu Thr
            210                 215                 220

Ser Ser Tyr Phe Thr Ile Arg Ala Ile Asp Tyr Val His Thr Leu His
    225                 230                 235                    240

Pro Gly Leu Val Tyr Leu Ile Ser Asp Pro Lys Trp Val Arg Lys
                    245                 250                 255

Gln Ile Ala Glu His Leu Asp Tyr His Asp Val Lys Ile Met Glu
                260                 265                 270

Thr Pro Ile Asn Ala Ala Ile Arg Asp Leu Tyr Phe Ser Gln Ala His
                275                 280                 285

Cys Asp Ser Val Leu Ile Thr Ala Pro Ser Ser Thr Phe Gly Trp Trp
    290                 295                 300

Ile Gly Tyr Met Ser Lys Asn Gln Ser Asn Val Tyr Tyr Arg Asp Ile
    305                 310                 315                    320

Gln Glu Thr Asp Asp Met Val Lys Tyr Lys Met Val Glu Glu Asp Phe
                    325                 330                 335

Phe Pro Pro Thr Trp Lys Lys Leu Gly Met Ser Arg Asn Gly Ser Ile
                340                 345                 350

Ile Ser Lys
            355

<210> SEQ ID NO 6
<211> LENGTH: 361
<212> TYPE: PRT
<213> ORGANISM: Caenorhabditis elegans

<400> SEQUENCE: 6

Met Asp Pro Leu Gly Ala Ala Lys Pro Gln Trp Pro Trp Arg Arg Cys
    1               5                  10                 15
```

```
Leu Ala Ala Leu Leu Phe Gln Leu Leu Val Ala Val Cys Phe Phe Ser
            20                  25                  30

Tyr Leu Arg Val Ser Arg Asp Asp Ala Thr Gly Ser Pro Arg Ala Pro
            35                  40                  45

Ser Gly Ser Ser Arg Gln Asp Thr Thr Pro Thr Arg Pro Thr Leu Leu
    50                  55                  60

Ile Leu Leu Trp Thr Trp Pro Phe His Ile Pro Val Ala Leu Ser Arg
65                  70                  75                  80

Cys Ser Glu Met Val Pro Gly Thr Ala Asp Cys His Ile Thr Ala Asp
                85                  90                  95

Arg Lys Val Tyr Pro Gln Ala Asp Thr Val Ile Val His His Trp Asp
                100                 105                 110

Ile Met Ser Asn Pro Lys Ser Arg Leu Pro Pro Ser Pro Arg Pro Gln
            115                 120                 125

Gly Gln Arg Trp Ile Trp Phe Asn Leu Glu Pro Pro Asn Cys Gln
            130                 135                 140

His Leu Glu Ala Leu Asp Arg Tyr Phe Asn Leu Thr Met Ser Tyr Arg
145                 150                 155                 160

Ser Asp Ser Asp Ile Phe Thr Pro Tyr Gly Trp Leu Glu Pro Trp Ser
                165                 170                 175

Gly Gln Pro Ala His Pro Pro Leu Asn Leu Ser Ala Lys Thr Glu Leu
                180                 185                 190

Val Ala Trp Ala Val Ser Asn Trp Lys Pro Asp Ser Ala Arg Val Arg
                195                 200                 205

Tyr Tyr Gln Ser Leu Gln Ala His Leu Lys Val Asp Val Tyr Gly Arg
                210                 215                 220

Ser His Lys Pro Leu Pro Lys Gly Thr Met Met Glu Thr Leu Ser Arg
225                 230                 235                 240

Tyr Lys Phe Tyr Leu Ala Phe Glu Asn Ser Leu His Pro Asp Tyr Ile
                245                 250                 255

Thr Glu Lys Leu Trp Arg Asn Ala Leu Glu Ala Trp Ala Val Pro Val
            260                 265                 270

Val Leu Gly Pro Ser Arg Ser Asn Tyr Glu Arg Phe Leu Pro Pro Asp
            275                 280                 285

Ala Phe Ile His Val Asp Asp Phe Gln Ser Pro Lys Asp Leu Ala Arg
            290                 295                 300

Tyr Leu Gln Glu Leu Asp Lys Asp His Ala Arg Tyr Leu Ser Tyr Phe
305                 310                 315                 320

Arg Trp Arg Glu Thr Leu Arg Pro Arg Ser Phe Ser Trp Ala Leu Asp
                325                 330                 335

Phe Cys Lys Ala Cys Trp Lys Leu Gln Gln Glu Ser Arg Tyr Gln Thr
                340                 345                 350

Val Arg Ser Ile Ala Ala Trp Phe Thr
            355                 360

<210> SEQ ID NO 7
<211> LENGTH: 365
<212> TYPE: PRT
<213> ORGANISM: Caenorhabditis elegans

<400> SEQUENCE: 7

Met Tyr Pro Pro Gly Cys Ala Lys Val Lys Cys Ser Trp His His Cys
1               5                   10                  15

Leu Pro Gly Leu Leu Leu Gln Leu Leu Leu Ala Leu Cys Phe Phe Ser
            20                  25                  30
```

```
Tyr Leu Arg Met Ser Gln Glu Lys Pro Lys Pro Met Trp Val
        35                  40                  45

Ser Glu Leu Gly Ala Pro Ser Gln Ala Thr Glu Gly Ser Ser Ala His
 50                      55                  60

Leu Pro Leu Arg Val Leu Leu Trp Thr Trp Pro Phe Asn Gln Pro Val
 65                  70                  75                  80

Ala Leu Ser Arg Cys Ser Glu Leu Trp Pro Gly Thr Ala Asp Cys Gln
                 85                  90                  95

Leu Thr Val Asn Arg Ser Glu Tyr Pro Gln Ala Asp Ala Val Phe Val
             100                 105                 110

His His Arg Glu Val Ser His Arg Pro Lys Met Gln Leu Pro Pro Ser
             115                 120                 125

Pro Arg Pro Ala Asp Gln Arg Trp Val Trp Phe Ser Met Glu Ser Pro
 130                 135                 140

Ser Asn Cys Leu Lys Leu Lys Asp Leu Asp Gly Tyr Phe Asn Leu Thr
145                 150                 155                 160

Met Ser Tyr Arg Arg Asp Ser Asp Ile Phe Met Pro Tyr Gly Trp Leu
                165                 170                 175

Glu Pro Trp Pro Ser Gln Pro Val Glu Thr Leu Leu Asn Ile Ser Ala
            180                 185                 190

Lys Thr Lys Leu Val Ala Trp Val Ser Asn Trp Asn Thr Asp Ser
        195                 200                 205

Ile Arg Val Gln Tyr Tyr Lys Leu Leu Lys Pro His Leu Gln Val Asp
        210                 215                 220

Val Tyr Gly Arg Phe His Thr Pro Leu Pro His Ala Leu Met Ala Lys
225                 230                 235                 240

Gln Leu Ser Gln Tyr Lys Phe Tyr Leu Ala Phe Glu Asn Ser Leu His
                245                 250                 255

Pro Asp Tyr Ile Thr Glu Lys Leu Trp Lys Asn Ala Leu Gln Ala Trp
            260                 265                 270

Ala Val Pro Val Val Leu Gly Pro Ser Arg Val Asn Tyr Glu Gln Phe
        275                 280                 285

Leu Pro Pro Lys Ala Phe Ile His Val Glu Asp Phe Gln Ser Pro Lys
290                 295                 300

Asp Leu Ala Gln Tyr Leu Leu Ala Leu Asp Lys Asp Tyr Ala Ser Tyr
305                 310                 315                 320

Leu Asn Tyr Phe Arg Trp Arg Glu Thr Leu Arg Pro Arg Ser Phe Ser
                325                 330                 335

Trp Ala Leu Met Phe Cys Lys Ala Cys Trp Lys Leu Gln Gln Glu Pro
            340                 345                 350

Arg Tyr Gln Thr Val Pro Ser Ile Ala Ser Trp Phe Gln
        355                 360                 365

<210> SEQ ID NO 8
<211> LENGTH: 393
<212> TYPE: PRT
<213> ORGANISM: Caenorhabditis elegans

<400> SEQUENCE: 8

Met Glu Leu Gly Pro Arg Trp Ser Pro Ala Ala Arg Pro Gly Cys Pro
 1               5                  10                  15

Arg Arg Trp Arg Arg Arg Trp Ala Leu Leu Gly Ala Leu Leu Gly Ala
             20                  25                  30

Ala Leu Ala Leu Tyr Val Cys Val Arg Glu Leu Arg Arg Arg Gly Ser
```

```
            35                  40                  45
Ala Gly Arg Pro Glu Gly Glu Val Thr Val Leu Leu Trp Trp Glu Pro
 50                  55                  60

Phe Gly Arg Pro Trp Arg Pro Ala Asp Cys Arg Arg Tyr Asn Ile
 65                  70                  75                  80

Thr Gly Cys Leu Leu Ser Ala Asp Arg Gly Tyr Gly Glu Ala Arg
                     85                  90                  95

Ala Val Leu Phe His His Arg Asp Leu Ala Leu His Gly Arg Gln Gly
                    100                 105                 110

Leu Pro Arg Gly Pro Pro Pro Pro Arg Gln Arg Trp Val Trp
                115                 120                 125

Met Asn Phe Glu Ser Pro Ser His Ser Pro Gly Leu Arg Gly Leu Ala
                130                 135                 140

Gly Leu Phe Asn Trp Thr Met Ser Tyr Arg Arg Asp Ser Asp Val Phe
145                 150                 155                 160

Val Pro Tyr Gly Tyr Leu Tyr Glu Pro Pro Ser Pro Arg Pro Phe Val
                165                 170                 175

Leu Pro Arg Lys Ser Arg Leu Val Ala Trp Val Ile Ser Asn Trp Asn
                180                 185                 190

Glu Glu His Ala Arg Val Arg Tyr Tyr Arg Gln Leu Lys Glu His Leu
                195                 200                 205

Pro Ile Asp Val Tyr Gly Ala Arg Gly Met Ala Leu Leu Glu Gly Ser
210                 215                 220

Val Val Lys Thr Val Ser Ala Tyr Lys Phe Tyr Leu Ala Phe Glu Asn
225                 230                 235                 240

Ser Gln His Thr Asp Tyr Ile Thr Glu Lys Leu Trp Lys Asn Ala Phe
                245                 250                 255

Ala Ala Ser Ala Val Pro Val Val Leu Gly Pro Arg Arg Ala Asn Tyr
                260                 265                 270

Glu Arg Phe Ile Pro Ala Asp Ser Phe Ile His Val Asp Asp Phe Pro
                275                 280                 285

Ser Pro Arg Leu Leu Ala Thr Tyr Leu Lys Phe Leu Asp Lys Asn Lys
                290                 295                 300

Pro Ser Tyr Arg Arg Tyr Phe Ala Trp Arg Asn Lys Tyr Glu Val His
305                 310                 315                 320

Val Thr Ser Phe Trp Asp Glu His Tyr Cys Lys Val Cys Glu Ala Val
                325                 330                 335

Arg Thr Ala Gly Asn Gln Leu Lys Thr Val Gln Asn Leu Ala Gly Trp
                340                 345                 350

Phe Glu Ser Val Cys Arg Met Ala Trp Thr Glu Pro Arg Gln Lys Val
                355                 360                 365

Leu Ile Pro Asn Trp Asp Ala Tyr Trp Arg Gln Thr Cys Glu Lys Asp
                370                 375                 380

Gly Thr Leu Val Asp Ser Ile Pro Asp
385                 390

<210> SEQ ID NO 9
<211> LENGTH: 450
<212> TYPE: PRT
<213> ORGANISM: Caenorhabditis elegans

<400> SEQUENCE: 9

Met Lys Lys Gln Asn Thr Pro Arg Val Phe Gly Tyr Tyr Ala Thr Ser
 1               5                  10                  15
```

-continued

```
Cys Arg Trp Leu Gly Val Asp Asp Arg Phe Leu Arg Phe Leu Trp Lys
             20                  25                  30

Tyr Leu Met Phe Ala Cys Cys Ile Thr Tyr Leu Leu Val Ile Tyr Ala
             35                  40                  45

Pro Ile Ser Lys Ser Glu Gln Lys Asp Trp Lys Glu Gly Glu Ile Glu
             50                  55                  60

Leu Ser Asn Asp His Glu Leu Asp Val Pro Ile Leu Gln Lys Glu Glu
 65                  70                  75                  80

Leu Lys Pro Gln Gln Arg Pro Ser Phe Glu Glu Asn Val Pro Lys Lys
                     85                  90                  95

Lys Thr Phe Asn Phe Asn Pro Val Gly Lys Glu Pro Phe Asp Val Glu
             100                 105                 110

Glu Val Leu Thr Ser Ser Asp Ile Lys Leu Glu Glu Arg Met Thr Ala
             115                 120                 125

Thr Val Ile Pro Gly Gln Lys Arg Leu Ile Leu Ser Trp Asn Ala Gly
             130                 135                 140

His Ser Gln Asp Asn Leu Gln Gly Cys Pro Asp Trp Asn Cys Glu Phe
145                 150                 155                 160

Thr Gln Val Arg Ala Arg Ala Pro Asp Ala Asp Ala Val Leu Ile Ala
             165                 170                 175

His Met Asp Asn Asp Phe Val Pro Lys Pro Asn Gln Tyr Val Val Tyr
             180                 185                 190

Phe Ser Gln Glu Ser Pro Ala Asn Ser Gly Ile Gln Ile Pro Arg Pro
             195                 200                 205

Asp Tyr Ile Asn Met Thr Leu Gly Phe Arg His Asp Thr Pro Ala Gly
             210                 215                 220

Ser Pro Tyr Gly Tyr Thr Val Lys Leu Gly Ala Lys Ser Arg Lys Thr
225                 230                 235                 240

Gly Gln Val Val Asp Ala Asn Leu Val Asn Gly Lys Ala Lys Gly Ala
             245                 250                 255

Ala Trp Phe Val Ser His Cys Gln Thr Asn Ser Lys Arg Glu Asp Phe
             260                 265                 270

Val Lys Lys Leu Gln Lys His Leu Gln Ile Asp Ile Tyr Gly Gly Cys
             275                 280                 285

Gly Pro Met Lys Cys Ala Arg Gly Asp Ser Lys Cys Asp Thr Met Leu
             290                 295                 300

Asp Thr Asp Tyr His Phe Tyr Val Thr Phe Glu Asn Ser Ile Cys Glu
305                 310                 315                 320

Asp Tyr Val Thr Glu Lys Leu Trp Lys Ser Gly Tyr Gln Asn Thr Ile
             325                 330                 335

Ile Pro Leu Val Leu Lys Arg Lys Leu Val Glu Pro Phe Val Pro Pro
             340                 345                 350

Asn Ser Phe Ile Ala Ile Asp Asp Phe Lys Ser Val Lys Glu Met Gly
             355                 360                 365

Asp Tyr Leu Asn Tyr Leu Met Asn Asn Lys Thr Ala Tyr Met Glu Tyr
             370                 375                 380

Phe Glu Trp Arg His Asp Tyr Lys Val Val Phe Leu Asp Gly Ser His
385                 390                 395                 400

His Asp Val Leu Glu Arg Pro Trp Gly Phe Cys Gln Val Cys Arg Met
             405                 410                 415

Ala Trp Thr Glu Pro Arg Gln Lys Val Leu Ile Pro Asn Trp Asp Ala
             420                 425                 430

Tyr Trp Arg Gln Thr Cys Glu Lys Asp Gly Thr Leu Val Asp Ser Ile
```

```
                  435               440               445
Pro Asp
    450

<210> SEQ ID NO 10
<211> LENGTH: 126
<212> TYPE: DNA
<213> ORGANISM: Caenorhabditis elegans

<400> SEQUENCE: 10
ggcgtggacg acagattcct tcgcttttg tttctatttt attttgttttt tttgcaggtc    60 taattactcc ggatgactgc aagaagcatc aaactttcct ttgcaagatg gaaatattta   120
atgttt                                                              126

<210> SEQ ID NO 11
<211> LENGTH: 10
<212> TYPE: PRT
<213> ORGANISM: Caenorhabditis elegans

<400> SEQUENCE: 11

Gly Val Asp Asp Arg Phe Leu Arg Phe Leu
  1               5                  10

<210> SEQ ID NO 12
<211> LENGTH: 6
<212> TYPE: PRT
<213> ORGANISM: Caenorhabditis elegans

<400> SEQUENCE: 12

Trp Lys Tyr Leu Met Phe
  1               5

<210> SEQ ID NO 13
<211> LENGTH: 18
<212> TYPE: DNA
<213> ORGANISM: Artificial Sequence
<220> FEATURE:
<223> OTHER INFORMATION: Forward Primer

<400> SEQUENCE: 13
ctcaaatgcc tttccacc                                                  18

<210> SEQ ID NO 14
<211> LENGTH: 24
<212> TYPE: DNA
<213> ORGANISM: Artificial Sequence
<220> FEATURE:
<223> OTHER INFORMATION: Reverse Primer

<400> SEQUENCE: 14
caactaatct aacggaatag aatc                                           24

<210> SEQ ID NO 15
<211> LENGTH: 30
<212> TYPE: DNA
<213> ORGANISM: Artificial Sequence
<220> FEATURE:
<223> OTHER INFORMATION: Forward Primer

<400> SEQUENCE: 15
ttactgacaa catgaaaaaa caaaacactc                                     30

<210> SEQ ID NO 16
```

<211> LENGTH: 30
<212> TYPE: DNA
<213> ORGANISM: Artificial Sequence
<220> FEATURE:
<223> OTHER INFORMATION: Reverse Primer

<400> SEQUENCE: 16
atatttccat aaaaagcgaa ggaatctgtc                                    30

<210> SEQ ID NO 17
<211> LENGTH: 35
<212> TYPE: DNA
<213> ORGANISM: Artificial Sequence
<220> FEATURE:
<223> OTHER INFORMATION: Forward Primer

<400> SEQUENCE: 17
ttccttcgct ttttatggaa atatttaatg tttgc                              35

<210> SEQ ID NO 18
<211> LENGTH: 31
<212> TYPE: DNA
<213> ORGANISM: Artificial Sequence
<220> FEATURE:
<223> OTHER INFORMATION: Reverse Primer

<400> SEQUENCE: 18
actaatctaa cggaatagaa tctactagtg t                                  31

<210> SEQ ID NO 19
<211> LENGTH: 27
<212> TYPE: DNA
<213> ORGANISM: Artificial Sequence
<220> FEATURE:
<223> OTHER INFORMATION: Forward Primer

<400> SEQUENCE: 19
acaacatgaa aaacaaaac actcctc                                        27

<210> SEQ ID NO 20
<211> LENGTH: 27
<212> TYPE: DNA
<213> ORGANISM: Artificial Sequence
<220> FEATURE:
<223> OTHER INFORMATION: Reverse Primer

<400> SEQUENCE: 20
ctaatctaac ggaatagaat ctactag                                       27

<210> SEQ ID NO 21
<211> LENGTH: 19
<212> TYPE: DNA
<213> ORGANISM: Artificial Sequence
<220> FEATURE:
<223> OTHER INFORMATION: Forward Primer

<400> SEQUENCE: 21
aaccagttgt cgttggctc                                                19

<210> SEQ ID NO 22
<211> LENGTH: 26
<212> TYPE: DNA

```
<213> ORGANISM: Artificial Sequence
<220> FEATURE:
<223> OTHER INFORMATION: Reverse Primer

<400> SEQUENCE: 22
gagcataaat aacaagaaga tatgtg                                        26
```

What is claimed is:

1. A purified and isolated nucleic acid segment consisting essentially of a nucleic acid segment encoding enzymatically active α1,3-fucosyltransferase from *Caenorhabditis elegans*.

2. A purified and isolated nucleic acid segment consisting essentially of a nucleic acid segment encoding enzymatically active α1,2-fucosyltransferase from *Caenorhabditis elegans*.

3. A purified and isolated nucleic acid segment comprising a nucleotide sequence of SEQ ID NO:1 which encodes *Caenorhabditis elegans* α1,3-fucosyltransferase.

4. A purified and isolated nucleic acid segment which encodes *Caenorhabditis elegans* α1,3-fucosyltransferase and which is seventy-five percent (75%) homologous to the nucleotide sequence of claim 3.

5. A purified and isolated nucleic acid segment comprising a nucleotide sequence of SEQ ID NO:2 which encodes *Caenorhabditis elegans* α1,2-fucosyltransferase.

6. A purified and isolated nucleic acid segment which encodes *Caenorhabditis elegans* α1,2-fucosyltransferase and which is seventy-five percent (75%) homologous to the nucleotide sequence of claim 5.

7. A purified and isolated nucleic acid segment which encodes *Caenorhabditis elegans* α1,3-fucosyltransferase or *Caenorhabditis elegans* α1,2-fucosyltransferase, wherein the nucleic acid is selected from the group consisting of:
(a) a nucleotide sequence of SEQ ID NO:1;
(b) a nucleotide sequence of SEQ ID NO: 2; or
(c) a nucleotide sequence which is seventy-five percent (75%) homologous to the nucleotide sequences of (a) or (b).

8. A recombinant vector selected from the group consisting of a plasmid, cosmid, phage, or virus vector and wherein the recombinant vector further comprises a purified and isolated nucleic acid consisting essentially of a nucleic acid segment encoding enzymatically active α1,3-fucosyltransferase from *Caenorhabditis elegans*.

9. A recombinant vector selected from the group consisting of a plasmid, cosmid, phage, or virus vector and wherein the recombinant vector further comprises a purified and isolated a nucleic acid segment encoding enzymatically active α1,2-fucosyltransferase from *Caenorhabditis elegans*.

10. A recombinant host cell, wherein the recombinant host cell is a prokaryotic cell transformed or an eukaryotic cell transfected with a recombinant vector comprising a purified and isolated a nucleic acid segment consisting essentially of a nucleic acid segment encoding enzymatically active α1,3-fucosyltransferase from *Caenorhabditis elegans*.

11. The recombinant host cell of claim 10 wherein the cell produces α1,3-fucosyltransferase.

12. The recombinant host cell of claim 11 wherein the enzymatically active α1,3-fucosyltransferase is capable of fucosylating a protein, peptide or carbohydrate requiring fucosylation.

13. A recombinant host cell, wherein the recombinant host cell is a prokaryotic cell transformed or an eukaryotic cell transfected with a recombinant vector comprising a purified and isolated nucleic acid consisting essentially of a nucleic acid segment encoding enzymatically active α1,2-fucosyltransferase from *Caenorhabditis elegans*.

14. The recombinant host cell of claim 13 wherein the cell produces α1,2-fucosyltransferase.

15. The recombinant host cell of claim 14 wherein the enzymatically active α1,2-fucosyltransferase is capable of fucosylating a protein, peptide or carbohydrate requiring fucosylation.

16. A recombinant vector selected from the group consisting of a plasmid, cosmid, phage, or virus vector and wherein the recombinant vector further comprises a purified and isolated nucleic acid of SEQ ID NO:1 which encodes *Caenorhabditis elegans* α1,3-fucosyltransferase.

17. A recombinant vector selected from the group consisting of a plasmid, cosmid, phage, or virus vector and wherein the recombinant vector further comprises a purified nucleic acid of SEQ ID NO:2 which encodes *Caenorhabditis elegans* α1,2-fucosyltransferase.

18. A recombinant host cell, wherein the recombinant host cell is a prokaryotic cell transformed or an eukaryotic cell transfected with a recombinant vector comprising a purified and isolated nucleic acid sequence of SEQ ID NO:1 which encodes an enzymatically active *Caenorhabditis elegans* α1,3-fucosyltransferase.

19. The recombinant host cell of claim 18 wherein the cell produces *Caenorhabditis elegans* α1,3-fucosyltransferase.

20. The recombinant host cell of claim 19 wherein the enzymatically active *Caenorhabditis elegans* α1,3-fucosyltransferase is capable of fucosylating a protein, peptide or carbohydrate requiring fucosylation.

21. A recombinant host cell, wherein the recombinant host cell is a prokaryotic cell transformed or an eukaryotic cell transfected with a recombinant vector comprising a purified and isolated nucleic acid sequence of SEQ ID NO:2 which encodes an enzymatically active *Caenorhabditis elegans* α1,2-fucosyltransferase.

22. The recombinant host cell of claim 21 wherein the cell produces *Caenorhabditis elegans* αb 1,2-fucosyltransferase.

23. The recombinant host cell of claim 22 wherein the enzymatically active *Caenorhabditis elegans* α1,2-fucosyltransferase is capable of fucosylating a protein, peptide or carbohydrate requiring fucosylation.

24. A procaryotic or eucaryotic host cell transformed or transfected with a nucleic acid segment in a manner allowing the host cell to express *Caenorhabditis elegans* α1,3-fucosyltransferase or *Caenorhabditis elegans* α1,2-fucosyltransferase, wherein said nucleic acid segment comprises the nucleic acid segment of SEQ ID NO:1 or SEQ ID NO:2.

25. A method for detecting a DNA species, the method comprising the steps of:
   (a) obtaining a DNA sample;
   (b) contacting the DNA sample with a purified nucleic acid segment of SEQ ID NO:1 or SEQ ID NO:2;
   (c) hybridizing the DNA sample and the purified nucleic acid segment thereby forming a hybridized complex; and
   (d) detecting the complex.

26. A method for producing fucosyltransferase, the method comprising the steps of:
   (a) introducing a purified and isolated nucleic acid segment having a coding region of SEQ ID NO:1 or SEQ ID NO:2 which encodes an enzymatically active α1,3-fucosyltransferase or α1,2-fucosyltransferase into a host organism;
   (b) growing the host organism in a medium to produce α1,3-fucosyltransferase or α1,2-fucosyltransferase; and
   (c) recovering and purifying the produced α1,3-fucosyltransferase or α1,2-fucosyltransferase.

27. A process for producing fucosyltransferase, the process comprising the steps of:
   (a) culturing a host cell transformed or transfected with a vector containing at least one purified and isolated polynucleotide of SEQ ID NO:1 or SEQ ID NO:2 which encodes an enzymatically active *Caenorhabditis elegans* α1,3-fucosyltransferase or *Caenorhabditis elegans* α1,2-fucosyltransferase into a host organism;
   (b) expressing a α1,3-fucosyltransferase or α1,2-fucosyltransferase enzyme; and
   (c) purifying the α1,3-fucosyltransferase or α1,2-fucosyltransferase from the cultured host cell.

28. The process of claim 27 wherein in step (b), the α1,3-fucosyltransferase or α1,2-fucosyltransferase is soluble.

* * * * *